United States Patent [19]

Sikorska et al.

[11] Patent Number: 5,626,830
[45] Date of Patent: May 6, 1997

[54] ANTI-MYOSIN MOUSE MONOCLONAL ANTIBODY AND METHOD OF USE FOR DIAGNOSIS OF MYOCARDIAL INFARCTION

[75] Inventors: Hanna Sikorska, Ile Bizard; Sylvine Savoie, Montréal; Clémence Desputeau, Bellefeuille, all of Canada

[73] Assignee: Biotech Cardio-Vision, Societe en Commandite Enregistree, Montreal, Canada

[21] Appl. No.: 251,813

[22] Filed: May 31, 1994

Related U.S. Application Data

[63] Continuation-in-part of Ser. No. 905,526, Jun. 29, 1992, abandoned, which is a continuation of Ser. No. 327,747, Mar. 23, 1989, abandoned.

[51] Int. Cl.$^6$ .................. A61K 51/10; C12N 15/20; A07K 16/18
[52] U.S. Cl. ............. 424/1.49; 530/388.2; 530/388.25; 530/391.3
[58] Field of Search ................ 530/388.2, 388.25, 530/391.3; 435/240.27; 424/1.49, 9

[56] References Cited

U.S. PATENT DOCUMENTS 4,943,427  7/1990  Yazaki et al. .

OTHER PUBLICATIONS

Goodwin, J Nucl. Med 28:1358–1362, 1987.
Bouvagnet et al. Circ Res 1984; 55: 794–804.
Bouvagnet et al. Circ Res 1987; 61: 329–336.
Bottrick et al. Circulation 1986; 74: 477–483.
Chizzonite et al. J Biol Chem 1982; 257: 2056–2065.
Clark et al. J. Biol Chem 1982; 257: 5449–5454.
Dechesne et al. J. Mol. Cell Cardiol. 1985; 17: 753–768.
Dechesne et al. J. Cell Biol. 1987; 105: 3031–3038.
Ebrechl et al. Basic Res Cardiol 1982; 77: 220–234.
Essen et al. Am. J. Physiol. 1988; 255: H659–H663.
Everett et al. J. Biol. Chem. 1983; 258: 2421–2425.
Feir et al. Am. J. Physiol. 1984; 247: H817–H823.
Flink et al. J. Biol. Chem 1979; 254: 3105–3110.
Geenen et al. Am J Physiol 1989; 256: H745–H750.
Hoffman et al. Basic Res Cardiol 1987a; 32; 359–369.
Hoffman et al. Biomed Biochem Acta 1987b; 46: S724–S727.
Hoh et al. J Mol Cell Cardiol 1977; 10: 1053–1076.
Hoh et al. J Mol Cell Cardio 1978; 10: 1053–1076.
Hoh et al. FEBS Lett 1979; 97: 330–334.
Komuro et al. J Biol Chem 1986; 261: 4504–4509.
Kurabayashi et al. J Clin Invest 1988; 82: 524–531.
Litten et al. British J Radiol 1989; 62: 189–191.
Lompve et al. Nature 1979; 282: 105–107.
Lompre et al. J Biol Chem 1984; 259: 6437–6446.
Mahdavi et al. Nature 1982; 297: 659–664.
Mahdavi et al. Proc Natl Acad Sci USA 1984; 81: 2626–2630.
Malhotra et al., Circ Res 1981; 49: 1243–1250.
Malhotra et al., Circulation 1983; 68: 111–7.
Mercadier et al., Circ Res 1981; 49: 525–532.
Movano et al., J Mol Cell Cardiol 1988; 20: 875–886.
Morris et al., Am J Physio 1989; 256: R976–R981.
Pauletto et al. Hypertension 1989; 14: 556–562.
Samvel et al., Circ Res 1983; 52: 200–209.
Sartore et al., J Cell Biol. 1981; 88: 226–233.
Schevere et al., J Clin Invest 1982; 70: 1300–1305.
Schlessinger et al., Biochem Int 1985; 11: 747–755.
Schwartz et al., J Mol Cell Cardiol 1981; 13: 1071–1075.
Tsuchimochi et al., J Clin Invest 1984; 74: 662–665.
Tsuchimochi et al., Jpn Circ J 1986; 50: 1044–1052.
Tsuchimochi et al., J Clin Invest 1988; 81: 110–118.
Whalen et al., Proc Natl Acad Sci USA 1979; 76: 5197–5201.
Takihara et al., P. N. A. S. 1989; 86: 3504–3508.
Alpert & Mulieri, Med. Sci. Sports Exerc., 18, 309–313 (1986).
Alpert et al., Circ. Res., 50, 491–500, (1982).
Alpert et al., Fed. Proc. 41, 192–198, (1981).
Dillman, et al., J. Biol. Chem., 259, 2035–2038, (1984).
Gorza et al., Circ. Res., 54, 694–702 (1984).
Hirayama et al., Clin. Biochem., 23:515–522 (1990).
Hirzel et al., Circ. Res., 57, 729–740 (1985).
Izumo, et al., Science, 231, 597–600, (1986).
Katus et al., Am. J. Cardiol., 54:964–970 (1984).
Kissling et al., Basic Res. Cardiol., 77, 255–270, (1982).
Kohler et al., Nature, 256, 495 (1975).
Kuro–O et al., J. Clin. Invest., 77, 340–347 (1986).
Laemmli, Nature, 227, 680–685, (1970).
Larue et al., Clin. Chem., 37: 78–82 (1991).
Léger et al., Am. Heart J., 120:781–790 (1990).
Léger et al., Eur. J. Clin. Invest., 15:422–429 (1985).
Margossian and Lowey, Methods in Enzymol., 85:55–71 (1982).
Masaki et al., J. Biochem., 76, 441, (1974).
McNally et al., J. Mol. Biol., 210:665–671 (1989).
Sikorska et al., Nucl. Med. Biol., 17:567–584 (1990).
Swynghedauw, Physiol. Rev., 66, 710–771, (1986).
Tobacman et al, J. Biol. Chem., 259, 11226–11230, (1984).
Weeds et al., Nauture, 257:54 (1975).
Yasaki et al., Circ. Res., 35, 15, (1974).

*Primary Examiner*—Paula K. Hutzell
*Attorney, Agent, or Firm*—Klauber & Jackson

[57] ABSTRACT

A monoclonal antibody or antigen binding fragment thereof which recognizes light meromyosin fragments of α- and β-type human cardiac myosin heavy chains that remain in situ after myocardial cell death is described. The antibody is produced by the hybridoma having the accession number ATCC HB9916. The antibody or antigen binding fragment thereof does not cross-react with human myosin light chains. The monoclonal antibody or antigen binding fragment thereof, in a labeled form is capable of producing an image of both ventricular and atrial damage resulting from myocardial cell necrosis and is capable of producing an image of a cell or tissue expressing myosin.

10 Claims, 11 Drawing Sheets
(4 of 11 Drawing(s) in Color)

Scintiscan of a dog injected with AM F(ab')$_2$-DTPA-$^{111}$In (2 mCi, 400 μg) The image was obtained 21 h after i.v. administration of the $^{111}$In preparation and 24 h after artery occlusion. The infarcted area of the heart is clearly delineated above the liver.

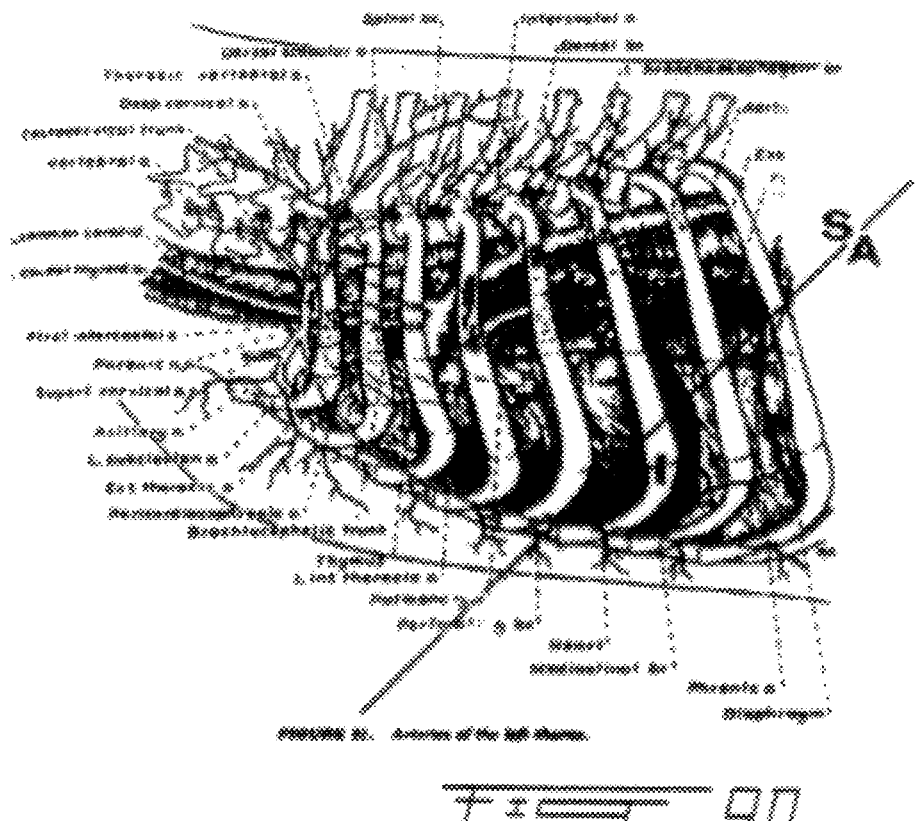

ANTI-MYOSIN MOUSE MONOCLONAL ANTIBODY AND METHOD OF USE FOR DIAGNOSIS OF MYOCARDIAL INFARCTION

RELATED APPLICATIONS

This application is a continuation-in-part of application Ser. No. 07/905,526 filed on Jun. 29, 1992, now abandoned, which is a continuation of application Ser. No. 07/327,747 filed on Mar. 23, 1989, which is now abandoned.

BACKGROUND OF THE INVENTION

One of the most interesting aspects of modern cell biology is the mechanism by which cells and tissues respond to various kinds of stress. For the heart this response is especially important, because the changing demands induce a protection which is essential for survival. A temporary stimulation of the heart is regulated by changes in diastolic volume (preload), aortic pressure (afterload), heart rate, adrenergic mechanism, and substrate availability. If the increase in demand is chronic the response leads to the development of adaptional factors. Two processes are of importance: i) hypertrophy due to an increase in the size of the myocytes and ii) an elevated efficiency of the contraction of each sarcomere. The restructuring of the different components of the cell depends on the nature, duration, and intensity of the stress, as well as on the age and the species (N. R. Alpert, L. A. Mulieri, Med. Sci. Sports Exerc., 18, 309–313 (1986)). This is particularly true for muscle cells. Muscles are classified broadly into the two groups of striated muscles and smooth muscles. Striated muscles are further classified into cardiac muscles and skeletal muscles, the skeletal muscles being further classified into fast muscles and slow muscles. It has been reported that these can be distinguished immunochemically through the difference in immunogenicity of the myosin molecules which are major constituents of muscles (Masaki et al., J. Biochem., 76, 441, (1974)). At least two molecular variants of myosin heavy chains, coded by distinctive genes (V. Mahdavi, V. A. P. Chambers, B. Nadal-Ginard, Proc. Natl. Acad. Sci. USA., 81, 2626–2630 (1984)), have been described in the human myocardium: an atrial HCα- and a ventricular HCβ-type (L. Gorza, J. J. Mercadier, K. Schwartz, L. E. Thornell, S. Satore, S. Schiaffino, Circ. Res., 54, 694–702 (1984); J. J. Mercadier, P. Bouveret, L. Gorza, S. Schiaffino, W. A. Clark, R. Zak, B. Swynghedauw, J. Schwartz, Circ. Res., 53, 52–63 (1983); H. O. Hirzel, C. R. Tuchschmid, J. Schneider, H. P. Krayenbuehl, M. C. Schaub, Circ. Res., 57, 729–740 (1985); M. Kuro-O, H. Tsuchimochi, Uedas, F. Takaku, Y. Yazaki, J. Clin. Invest., 77, 340–347 (1986); H. Tsuchimochi, M. Kuro-O, F. Takaku, K. Yoshida, M. Kawana, S. Kimata, Y. Yazaki, Jap. Circ. J., 50, 1044–1052 (1986); C. Dechesne et al., J. Mol. Cell. Cardiol., 17, 753–767 (1985); P. Bouvagnet et al., Circ. Res., 55, 794–804 (1984); H. Tsuchimochi et al., J. Clin. Invest. 81, 110–118, (1988)).

They differ in both ATPase activity and mobility in pyrophosphate polyacrylamide gel electrophoresis. HCα has a higher $Ca^{++}$- and actin-activated ATPase activity than does HCβ and migrates faster in gels (Yasaki et al., Circ. Res., 35, 15, (1974); Hoh et al., J. Mol. Cell. Cardiol., 10 1053–1076, (1978)).

These two types of heavy chains have been shown in animals to form myosin molecules composed either of an αα homodimer or an αβ-heterodimer, or a ββ-homodimer which correspond to the V-1, V-2 and V-3 isoforms described by Hoh and coworkers (J. F. Y. Hoh, J. Mol. Cell Cardiol., 10, 1053–1076, (1978)). V-1 exhibits higher adenosine triphosphatase (ATPase) activity than V-3.

The ratio of these myosin isoforms varies according to the physiological and pathological state or developmental stage of the myocardium (for reviews, see Mercadier et al., Circ. Res., 53, 52–62, (1983); Tobacman et al, J. Biol. Chem., 259, 11226–11230, (1984)). The change from V-1 toward V-3 is accompanied by a decrease in ATPase activity and speed of contraction (Schwartz et al., J. Mol. Cell Cardiol., 13, 1071–1078, (1981); Ebrecht et al., Basic Res. Cardiol., 77, 220–234, (1982)), an improved economy of force generation (Alpert et al., Fed. Proc. 41, 192–198, (1981); Alpert et al., Circ. Res., 50, 491–500, (1982)), and decreased oxygen consumption (Kissling et al., Basic Res. Cardiol., 77, 255–270, (1982)). These changes in myosin HC composition found in animals were interpreted as an adaptation of the myocardial cell, together with compensatory hypertrophy of the muscle, to new functional requirements.

In man, normal ventricular tissue contains predominantly the V-3 species (ββ-homodimer) and only few amounts (0–15%) of the V-1 species (αα-homodimer). The opposite is true for the human atrium, where the abundant myosin isoform is V-1 and, to a lesser degree, isozyme V-3.

Human fetal atrium is composed mostly of α-HC during the first 23 weeks of gestation. (Bouvagnet et al., Circ. Res., 61, 329–336, (1987)). β-HC is already expressed as traces at 14 weeks of gestation, and its expression increases progressively until birth, resulting in a great augmentation in β-HC. During this course, β-HC always predominates in certain areas (the crista terminalis and the interatrial septum) but not in other areas (the auricles). Preceding birth, the fetal ventricle is composed mostly of β-HC. From 14 weeks of gestation to birth, α-HC is expressed in very rare fibers. Then, after birth, a large number of fibers simultaneously synthesize α-HC.

Animal studies have shown evidence of thyroid hormone affecting the expression of isomyosin (for review, see B. Swynghedauw, Physiol. Rev., 66, 710–771, (1986)). It is not yet known whether the human heart has the same property, but at birth, increase of β-HC expression in the atrium and α-HC in the ventricle, is associated with the rapid rise in circulating thyroid hormone levels. Since Chizzonite and Zak (J. Biol. Chem., 259, 12628–12632, (1984)) have clearly demonstrated the role of thyroid hormone in the induction of α-HC expression in neonatal rat ventricle, thyroid hormone hypothetically could also induce ventricular α-HC expression in humans. Thyroid hormone has highly tissue specific effect and can switch HC gene expression on or off depending on the tissue where it is expressed (Izumo, et al., Science, 231, 597–600, (1986)). Insulin also is involved in the regulation of myosin HC expression (Dillman, et al., J. Biol. Chem., 259, 2035–2038, (1984)).

In pressure-overloaded human atrial muscle, there is a transition from α- to β-HC (Kurabayashi, et al., J. Clin. Invest., 82, 524–531, (1988); Tsuchimochi, et al., J. Clin. Invest., 74, 662–665, (1984)); Buttrick, et al., Circulation, 74, 477–483, (1986); Schlesinger, et al., Biochem. Intern. 11, 747–753, (1985)) as an early adaptation to the imposed load.

Myocardial infarction and associated work overload cause a transition in the light chain complements of the myosin (Hoffman, et al., Basic Res. Cardiol. 32, 359–369, (1987); Hoffman et al., Biomed. Biochem. Acta, 46, S724–S727, (1987)). Ventricular myosin light chains are found in pressure overloaded atria and atrial light chains have also been identified in the infarcted ventricle of the human heart. The relative proportions of atrial myosin heavy chains are changed after infarction. A decrease in β-HC and a corresponding increase in α-HC were observed. Ventricular hypertrophy in patients with coronary insufficiency induces α-HC expression. The relative part of this myosin type amounts to 20%.

In the field of muscle research, antibodies against muscle proteins have long been utilized.

In recent years, as a method for obtaining large amounts of an antibody having high specificity, it has been known to prepare a hybridoma, by fusion of an antibody-producing cell with a myeloma cell and culturing the hybridoma thus obtained to produce a monoclonal antibody (Kohler et al., Nature, 256, 495 (1975)), and a large number of monoclonal antibodies have been obtained by such a method.

Further, these antibodies can be labeled with radioisotopes and used for localization of myocardial infarction.

There is provided in U.S. Pat. No. 4,767,843 (Yazaki et al.) a monoclonal antibody which has specificity to cardiac myosin heavy chain α type but does not recognize cardiac myosin heavy chain β type and also a monoclonal antibody which has specificity to cardiac myosin heavy chain β type but does not recognize cardiac myosin heavy chain α type.

Although the fate of myosin following myocardial infarction is not exactly known, the published experimental evidence, allows one to expect that certain fragments of myosin remain in situ in myocyte while others are released to circulation. The classic light microscopic studies of the heart after myocardial infarction in man demonstrated that disappearance of muscle fibers is relatively slow, beginning about 6 hr after infarction and continuing for 2 to 6 weeks. While it has been reported that myosin with an intact ATPase activity can be extracted from infarcted muscle for as long as one month after acute infarction it has also been noted that there is a marked decrease in the amount of myosin in the infarcted zone within 24 to 48 hr of the infarct.

Among the potential causes of ischemia-induced cell damage is the acute intracellular acidosis that occurs after coronary artery occlusion. The decreased contractility of acutely ischemic myocardium and a decrease in actomyosin ATPase activity are the consequences of an acidosis.

Therefore, acidification of myosin due to ischemia could cause dissociation of light chains of myosin from heavy chains, and fragmentation of heavy chains, suggesting a possible source of circulating light chains and fragments of heavy chains after myocardial infarction. Ongoing release of myosin fragments could also be explained by proteolytic degradation of myofibrils by such enzymes as $Ca^{2+}$-activated proteinases, cathepsins B and D, and possibly cathepsins H and L. Thus, following myocardial infarction the free myosin is degraded by proteolytic enzymes or dissociated by the pH shift liberating more myosin fragments into circulation where they remain up to the 10-14th day after the onset of chest pain.

Several immunoassays for the quantitation of cardiac myosin light and heavy chain fragments in sera of patients with acute myocardial infarction (AMI) have been described and found useful in the diagnosis of AMI and estimation of infarct size (Katus et al., Am. J. Cardiol., 54:964-970 (1984); Hirayama et al., Clin. Biochem., 23:515-522 (1990); Léger et al., Eur. J. Clin. Invest., 15:422-429 (1985); Larue et al., Clin. Chem., 37: 78-82 (1991); Léger et al., Am. Heart J., 120:781-790 (1990)).

To detect circulating myosin heavy chain fragments, Léger et al. used murine monoclonal antibodies (MAbs) to the β-type myosin HC of human ventricle (Léger et al., Eur. J. Clin. Invest., 15:422-429 (1985)). However, not every anti-β myosin HC antibody is suitable for the recognition of circulating myosin HC, and thus for the measurement of myosin fragments in patients' plasma. Because in the circulation myosin is effectively proteolyzed into fragments as soon as it is liberated from the myocyte, only monoclonal antibodies that recognize those myosin fragments most resistant to proteolysis can be used in an assay. Chemotryptic subfragment 2 of the rod of heavy meromyosin (HMM) owing to the central position is very resistant to proteolysis. Thus, antibodies recognizing epitopes on the subfragment 2 of heavy meromyosin should be the best candidates for an assay detecting serum myosin fragments (Larue et al., Clin. Chem., 37: 78-82 (1991)).

On the contrary, antibodies directed to the subfragment 2 of heavy meromyosin are not the desirable candidates of in vivo imaging of AMI since they would cross-react with plasma myosin, causing high blood pool radioactive background. The only candidates for in vivo imaging are those antibodies that bind to myosin heavy chains that remain in situ after myocyte death and membrane disintegration, and only those that react with epitopes common to α and β-types of myosin HC.

Proteolytic enzymes dissociate myosin to light (LMM) and heavy (HMM) meromyosin fragments which can be further fragmented to subfragments 1 (SF1) and 2 (SF2) (Margossian and Lowey, Methods in Enzymol., 85:55-71 (1982)). LMM fragment of the rod is non-soluble in physiological fluids and is responsible for thick filament formation. The α and β MHC nucleotide and amino acid sequences are 97% identical in this region (Mahdavi et al., Proc. Natl. Acad. Sci. USA, 81:2626-2630 (1984); McNally et al., J. Mol. Biol., 210:665-671 (1989)).

In view of the above presented evidence, it would be highly desirable to have a monoclonal antibody which recognizes α- and β-heavy chain of atrial and ventricular human myosin for imaging of myocardial infarction, since a single antibody molecule would demarcate the infarcted zone regardless of the patient's age, the pathological or the physiological condition.

Thus, it would be highly desirable to be provided with antibodies directed to LMM fragment of cardiac myosin which may be the ideal candidates for AMI imaging.

Further, it would also be useful to have a monoclonal antibody which could provide the diagnosis of both atrial and ventricular myocardial infarction simultaneously.

SUMMARY OF THE INVENTION

Surprisingly and in accordance with the present invention, the 3-48 $G_5C_7$ antibody (ATCC HB9916) recognizes α- and β-type heavy chains of light meromyosin (LMM) fragment of cardiac myosin, it also reacts with LMM fragments of cardiac myosin and β-heavy chain of slow human skeletal muscle.

Further, the antibody of the present invention can be labeled with radioisotopes such as technetium-99 m, indium, iodine, etc., and applied for immunodetection, in which it is measured by whole-body gamma scintigraphy after administration into a patient, whereby localization of myocardial infarction is rendered possible.

More specifically, the present invention provides a monoclonal antibody which enables the diagnosis of both atrial and ventricular myocardial cell death by detecting only α- and β-type heavy chains of light meromyosin (LMM) fragment of cardiac myosin, and LMM fragments of cardiac myosin in situ.

The currently available techniques for diagnosis of myocardial infarction (MI) are not accurate enough to make a precise distinction between the necrotic and ischemic damage to myocardium. The adequate diagnosis is, however, essential for successful immediate treatment and a long-term survival of patients. The present invention intends to develop a new parameter that could assist the cardiologist in making the right diagnosis. The employed method involves the imaging of myosin heavy chains within the heart tissue using specific mouse monoclonal antibody tagged with radioisotope. This method is based on the principle that the cell death is caused by loss of membrane integrity. Intracellular enzymes leak to extracellular fluid and intracellular protein myosin is exposed to extracellular markers that are normally excluded from alive cells. Thus myosin becomes available to react with labeled antibodies or antibody fragments.

Myosin, the major muscle contractile protein, consists of two heavy chains each of about 200,000 daltons (d) and two pairs of light chains. Heavy chains form an α-helical coiled tail over a length of light chains. In ventricular myocardium light chain 1 is 27,000 d and light chain 2 is 20000 d. The intact molecule has a molecular weight of 500,000 daltons and due to heavy chains is soluble only in high salt solutions (>0.3M KCl). The catalytic and actin binding properties of myosin reside in the water-soluble heads. Both heavy and light chains of myosin derived from different species and tissues are structurally, enzymatically and antigenetically distinct.

Multiple molecular forms of myosin heavy chains have been demonstrated in fast, slow and embryonic skeletal muscle as well as in atria and ventricles of the myocardium. A single type of muscle may contain more than one molecular form of myosin heavy chain. Two isozymes, one being V-1 (α-chain) having a high ATPase activity and the other being V-3 (β-type) having a low ATPase activity exist in cardiac muscles. In humans, atrial muscles contain primarily α-type heavy chain while ventricular muscles contain substantially β-type chain.

This is a great improvement over the previous monoclonal antibodies, in that it enables the imaging of myocardial necrosis of both the atrial and ventricular region by using only one antibody, and that it will image the regions of the infarcted myocardium where transitions of myosin isozymes had occurred due to changes in either physiological or work-load conditions, and that it will not image the myosin fragments circulating in blood of infarcted patients.

BRIEF DESCRIPTION OF THE DRAWINGS

The file of this patent contains at least one drawing executed in color. Copies of this patent with color drawing (s) will be provided by the Patent and Trademark Office upon request and payment of the necessary tee.

FIGS. 9A–9D show SPECT imaging of an experimental canine infarct with FIG. 9(A) $^{99m}$Tc-AM 3–48 Fab', FIG. 9(B) $^{99m}$Tc-Sestamibi, FIG. 9(C) $^{99m}$Tc-pyrophosphate; and FIG. 9(D) Arteriae of the left thorax;

DETAILED DESCRIPTION OF THE INVENTION

Figure 1:
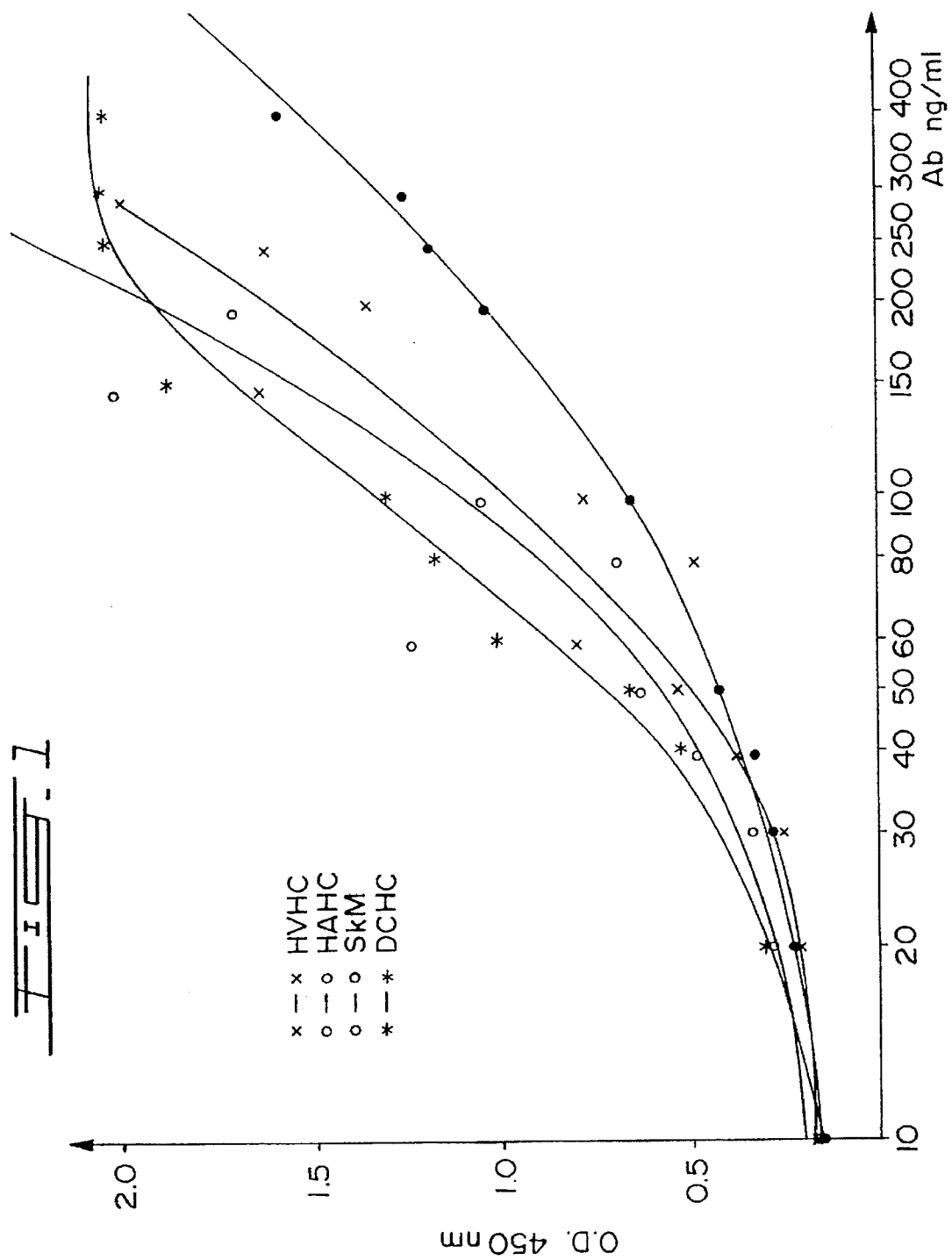
FIG. 1 shows the antibody dilution curves assayed in ELISA.

The antibody of the present invention can be distinguished from the antibodies known in the art in that it has the characteristic of being able to recognize 2 isozymes of cardiac myosin. A further useful characteristic of the antibody of the present invention is that it is capable of recognizing both α- and β-type heavy chains of light meromyosin (LMM) fragment of cardiac myosin, it also reacts with LMM fragments of cardiac myosin and β-heavy chain of slow human skeletal muscle. The monoclonal antibody of the invention has an affinity constant in the range of $1 \times 10^8$ to $9.9 \times 10^8$ $M^{-1}$ for both α- and β-type human cardiac myosin heavy chains.

The antibody of the present invention was obtained from the polyethylene glycol fusion of non-secreting mouse myeloma (P3×63.Ag8.653) cells with spleen cells from a Balb/c mouse immunized with human ventricular myosin. Hybrid cells were selected in HAT medium, tested for antigenic specificity in ELISA, and subcloned by limiting dilution four times. The hybridoma (ATCC HB9916) clone designated 3–48 $G_5C_7$ has been propagated in vitro, in a stationary phase monolayer tissue culture and is still stable after 112 passages. Antibody secreted to the tissue culture supernatant is concentrated and purified to homogeneity.

Both the primary cell seed and working cell bank are free of mycoplasma, viruses, bacteria and fungi. The cell line doubling time is 18.2 hrs and specific antibody secretion rate 70 μg IgG/ml medium/24 hrs. The antibody has been characterized with respect to its immunoglobulin class, isoelectric point, affinity, molecular weight and immunologic specificity.

The method for preparation of this hybridoma and the properties of the antibody of the present invention are described in detail below.

I- Obtaining hybridoma ATCC HB9916

1. Antigen Preparation, isolation and purification of cardiac myosin heavy chains from human or canine left ventricle All steps were performed at 4° C. Canine left ventricular muscle had been stored in 50% glycerol in 0.06M KCl, 0.02M KH$_2$PO$_4$ pH 6.5, 0.005M β-ME, 0.005M MgCl$_2$, 0.0002M PMSF. The tissue was minced in a cold meat grinder previously washed with 0.2M EDTA pH 7.0 and a resulting mince homogenized in 5 volumes of 0.05M KH$_2$PO$_4$ pH 6.8, 0.001M EDTA, 0.01M Na$_4$P$_2$O$_7$ pH 7.5, 0.001M DTT, 0.03M KCl, 0.01M MgCl$_2$, 0.0001M PMSF (solution 1) for 1 minute at 60 revolutions (27000 rpm) in Virtis 45™ homogenizer. The homogenate was centrifuged for 10 minutes at 8000 rpm (Sorvall GS-3™) and the pellet was washed once in 3 volumes of solution 1 and then once in 1% Triton™ in solution 1, followed by five washes in solution 1 to remove traces of Triton™. Each time the pellet was resuspended by brief (3 seconds) homogenization at 27000 rpm. The final pellet was homogenized in 400 ml of 0.1M $KH_2PO_4$, 0.3M KCl, 0.01M $Na_4P_2O_7$, 0.001M DTT, 0.001M EDTA, 0.05M $K_2HPO_4$, 0.005M $MgCl_2$, 0.0035M ATP, 0.0002M PMSF, 1 µg/ml pepstatin A, pH 7.5 and extraction continued for 15 minutes while stirring. Actomyosin containing supernatant obtained after centrifugation for 15 minutes at 8000 rpm (Sorvall GS-3™) was filtered through a cheese cloth and spun again for 20 minutes at 9000 rpm (Sorvall GS3™). The actomyosin was precipitated from the supernatant with 9 volumes of $H_2O$, 0.001M EDTA and collected by centrifugation at 9000 rpm (Sorvall GS-3™) for 20 minutes. The pellet was resuspended by homogenization in a glass Poter™ homogenizer in 87 ml of 0.05M $Na_4P_2O_7$, pH 7.5, 0.001M DTT, 0.001M EDTA, 0.005M $MgCl_2$, 0.002M ATP, and protein concentration determined by extinction co-efficient ($E^{1\%}_{280nm}$ for myosin=5.6). The myosin solution was made 2 mg/ml and contaminants (actin and tropomyosin) precipitated with 34% $(NH_4)_2SO_4$, 0.001M EDTA, pH 6.8 for 30 minutes, stirring. The supernatant, containing myosin, was collected by centrifugation for 25 minutes at 10,000 rpm and precipitated again with 42% $(NH_4)_2SO_4$ for 30 minutes, stirring. This time the myosin containing precipitate was collected by centrifugation at 9000 rpm (Sorvall GS-3™) for 30 minutes. The pellet was resuspended in small volume of 0.05M Tris/HCl pH 7.5, 0.5M KCl, 0.001M DTT and dialyzed against 200 volumes of the same solvent overnight at 4° C., with three buffer changes. The dialysate was then spun at 10,000 rpm (Sorvall SS-34™) for 10 minutes and myosin containing supernatant precipitated with 9 volumes of $d.H_2O$, 0.001M EDTA. The formed precipitate was spun at 20,000 rpm (Sorvall SS-34™) for 15 minutes.

To isolate heavy chains of myosin, the pellet was resuspended in small volume of 8M urea, 0.001M DTT, 0.01M EDTA, 0.05M Tris, pH 7.5 and stirred for 2 hours at room temperature. Heavy chains were precipitated with 10 volumes of cold $d.H_2O$, 1 mM EDTA pH 7.5 overnight at 4° C. The pellet was collected by centrifugation at 20,000 rpm (Sorvall SS-34™) for 10 minutes, resuspended in small volume of 0.5M KCl, 0.05M Tris pH 7.5, 0.001M EDTA and dialyzed against the same buffer for 24 hours with 3 changes of buffer. Thus produced myosin was mixed with equal volume of cold glycerol and stored aliquoted at −20° C. Each purification step was monitored by mobility on SDS-PAGE.

2. Immunization protocol

Balb/c female mouse, 6 weeks old, was injected with human left ventricular muscle myosin in 0.6M KCl, 0.05M potassium phosphate pH 6.5 according to the following immunization schedule.

| Date | Time Interval | Immunogen | Dose | Route |
|---|---|---|---|---|
| 19-6-85 | 0 | (1) in CFA* | 100 µg(1)/100 µl + 100 µl CFA | i.p** |
| 27-06-85 | 1 week | (1) in IFA*** | 100 µg(1)/100 µl + 100 µl IFA | i.p. |
| 04-07-85 | 1 week | (1) in IFA | 100 µg(1)/100 µl + 100 µl IFA | i.p. |
| 22-07-85 | 18 days | (1) in IFA | 100 µIg(1)/100 µl + 100 µl IFA | i.p. |
| 12-02-86 | 7 months | (2) in CFA | 50 µg(2)/50 µl + 50 µl CFA | i.p. |
| 27-02-86 | 2 weeks | (2) in IFA | 50 µg(2)/50 µl + 50 µl IFA | i.p. |
| 14-03-86 | 2 weeks | (2) only | 100 µg(2)/100 µl + buffer | i.p. |
| 22-03-86 | 1 week | (2) in saline | 100 µg(2)/100 µl + saline − final boosting | i.v**** |

*CFA = complete Freund's adjuvant;
**i.p. = intraperitoneally;
***IFA = incomplete Freund's adjuvant;
****i.v. = intravenously
(1) Human left ventricular muscle myosin lot #3 (35% $(NH_4)_2SO_4$ cut in 50% glycerol, 0.6 M KCl, 0.05 M $K_2HPO_4$, pH 6.7). For injections 1 mg/ml protein stock was prepared in 0.6 M KCl, 0.05 M $K_2HPO_4$ pH 6.7. 1 ml of myosin at 1 mg/ml was emulsified with 1 ml of Freund's adjuvant (aqueous phase into oil).
(2) Human cardiac myosin heavy chains "Toronto" lot. Protein concentration: 3 mg/ml. For injections, 1 mg/ml stock solution was prepared by 1:3 dilution in 0.6 M KCl, 0.05 M $K_2HPO_4$ pH 6.7.

3. Hybridoma production and selection

As myeloma cells, cell lines originated from various animals such as mice, rats and humans can be used. The cell line preferably used was of the non-secretor type, more specifically P3×63.Ag8.653. Nucleated spleen cells of immunized Balb/c female mice ($1.1 \times 10^8$) were combined with myeloma cells ($1.1 \times 10^7$) at a ratio of 10:1 and fused with 50% polyethylene glycol (PEG) M. W. 4000 (Merck) containing 5% DMSO (ATCC) at pH 7.4. PEG was added gradually: 1 ml over 1 minute, left for 90 seconds at 37° C. and then diluted with serum-free medium to 25 ml.

After washing, the fused cells were resuspended in hypoxanthine-aminopterin-thymidine (HAT) selective medium (IMDM, Penicillin/Streptomycin, 2 mM L-glutamine, 1 mM sodium pyruvate, 0.1 mM non-essential amino acids, 0.025% insulin, 0.025% transferrin, 0.25 µg/ml sodium selenite, $5 \times 10^{-5}$M 2-mercaptoethanol, HAT, 15% fetal bovine serum (FBS)) supplemented with ECGS (CR-endothelial cell growth supplement) (100 µg/ml) at $1 \times 10^6$ viable cells/ml and distributed into 6 24-well Costar™ plates 1 ml/well. Each well contained $1 \times 10^5$ normal mouse spleen cells in 1 ml of HAT medium to serve as a feeder layer.

Seven days later the clones were fed by replacing half of the volume with fresh HAT medium. On day 10, the plates were observed for hybrid growth and growing ones selected for screening in ELISA against heavy chains of human cardiac myosin and human skeletal myosin.

Clones whose supernatants were positive for both antigens were transferred to a 25 cm² flask and then to a 75 cm² T-flask. The hybridoma was subcloned by limiting dilution four times in IMDM supplemented as above.

As a result, a hybridoma ATCC HB9916 cell line producing an antibody having the ability to recognize cardiac myosin heavy chain α-type and β-type and β-heavy chain of slow skeletal muscle was obtained. It was designated 3–48 $G_5C_7$.

4. Production of monoclonal antibody

The final subclone, ATCC HB9916, was grown in a stationary monolayer culture in IMDM 95%, fetal bovine serum 5%. The cultures were passaged once a week into a new flask and fed twice a week by removing the spent medium by centrifugation and resuspending the cell at $0.25\times10^6_c$/ml in fresh medium. On average, 600 ml of tissue culture supernatant was collected per week.

The hybridoma producing the 3–48 $G_5C_7$ antibody has been deposited at the American Type Culture Collection (ATCC, 12301 Parklawn Drive, Rockville, Md. 20852 USA) on Nov. 30, 1988 under deposit number ATCC HB9916. This deposit is available to be public upon the grant of a patent to the assignee, Rougier Inc., disclosing same. The deposit is also available as required by Foreign Patent laws in countries wherein counterpart applications are filed.

5. ELISA for anti-myosin monoclonal antibody

Screening of tissue culture supernatants for anti-myosin monoclonal antibody production was done in enzyme-linked immunosorbent assay (ELISA). Microtitration plates (Dynatech Immulon I™) were coated with 100 µl of human cardiac myosin heavy chains at 10 µg/ml in 0.05M sodium carbonate-bicarbonate buffer pH 9.6, for overnight at 4° C. The unbound antigen was washed off 4 times with Tris buffered saline pH 7.4 (TS), 0.05% Tween 20™ (TS-Tween™) and the remaining binding sites saturated with 1% bovine serum albumin (BSA) (250 µl/well) in TS for 1 hour at 37° C. After brief washing, the wells were incubated with 100 µl of tissue culture supernatants from growing hybrids for 1 hour at 37° C.. The unbound antibody was washed off four times with TS-Tween™ and horseradish peroxidase-conjugated anti-mouse IgG+IgM antiserum, diluted 1:5000 with TS-BSA, added (100 µl/well) for further 1 hour incubation at 37° C. The colorimetric reaction was developed upon the addition of 30% $H_2O_2$ at 1 µl /1 ml in 0.1M sodium citrate buffer pH 5.0 containing 0.1% o-phenyl-enediamine dihydrochloride, and the absorbance read at 450 nm.

6. Purification of immunoglobulin

Tissue culture supernatant of ATCC HB9916 hybridoma was five fold concentrated by ultrafiltration on PM 30™ membrane and precipitated with 50% saturated ammonium sulfate, pH 6.8 for 60 minutes at 4° C., stirring. The precipitate was collected by centrifugation at 8000 rpm for 20 minutes and resuspended in phosphate buffered saline (PBS). It was dialyzed against PBS for two days with 4 buffer changes and then filtered through 0.45 µm membrane and further dialyzed against protein A binding buffer (1.45M glycine, 3M NaCl, pH 9.4) overnight at 4° C. 250 mg protein in 5 ml of binding buffer was injected into Bio-Rad™ polymer protein A HPLC preparative column and IgG eluted with Bio-Rad™ protein A elution buffer pH 3.1 at 4 ml/min and 1 min (4 ml) fractions were collected.

The IgG containing fractions were pooled, neutralized with NaOH, concentrated by membrane ultrafiltration and dialyzed against 10 mM $NaH_2PO_4$, pH 6.8, 0.01 mM $CaCl_2$, 0.02% $NaN_3$ overnight at 4° C. (HPHT column buffer A). Subsequently, 4.6 mg IgG in 2 ml of HPHT column buffer A was injected into HPLC hydroxylapatite (HPHT) column and eluted at 1 ml/min with 0–60% gradient of buffer B: 350 mM $NaH_2PO_4$, pH 6.8, 0.01 mM $CaCl_2$, and 1 min (1 ml) fractions were collected.

The last peak, containing IgG was pooled, concentrated by membrane ultrafiltration and dialyzed overnight at 4° C. against 0.05M $Na_2SO_4$, 0.02M $NaH_2PO_4$, pH 6.8 buffer. Finally, 1.0 mg IgG in 1.0 ml of the above buffer was injected into HPLC TSK 250 gel permeation column and chromatographed for 11 minutes at 1.0 ml/min. The IgG containing fractions were then pooled, concentrated by membrane ultrafiltration and dialyzed against PBS. For storage, protein concentration was adjusted to 5 mg/ml by Lowry assay and IgG aliquoted at 5 mg per vial for lyophilization. Lyophilized IgG was stored at −20° C.

7. F(ab')$_2$ fragment isolation from IgG$_1$

Limited proteolysis of IgG with the enzyme pepsin has been widely used for the preparation of F(ab')$_2$ fragments. Because there is variation among individual monoclonal antibodies of each subclass with respect to the rate of digestion, such parameters as optimal pH and incubation period had to be determined experimentally to obtain maximum yields of F(ab')$_2$ fragments (and little intact IgG).

The production of F(ab')$_2$ from IgG$_1$ was studied as a function of: pH in the range of 3.5–4.2, time in the range of 1½–24 hours and enzyme-antibody ratio of 1:10–1:100. The digestions were performed at 37° C. at 1 mg IgG/ml. The digestion was stopped by adding 1/40 volume of 1M Tris HCl and raising pH to 8.0. The course of digestion was monitored by SDS-PAGE under non-reduced conditions and retention of antibody activity by serial dilutions in ELISA.

The rate of digestion increased as the pH was decreased; at pH 4.2 the reaction required 24 hours for completion and at pH 3.5, cleavage was complete after 8 hours. The optimal conditions for preparation of F(ab')$_2$ fragments were found to be 4 hour digestion at pH 3.9 and pepsin-IgG ratio of 1:50. Under those conditions F(ab')$_2$ fragments were obtained in 60% yield.

Traces of undigested IgG and Fc fragment were removed by a passage through the HPLC protein A column. The purified F(ab')$_2$ fragments of 3–48 IgG still retained their reactivity with cardiac myosin when assayed in ELISA and on cryostat sections of ventricular muscle by indirect immunofluorescence.

II- Characterization of mouse monoclonal anti-myosin antibody

1. Immunoglobulin class determination

The immunoglobulin isotype was determined by double immunodiffusion in 1% agarose against monospecific, commercially available anti-mouse immunoglobulin class and subclass specific antisera. The immunoglobulin class of the antibody is IgG$_1$/k.

2. Determination of affinity constant of IgG

The equilibrium constant of reaction between antibody secreted by the hybridoma ATCC HB9916 and heavy chains of canine cardiac myosin (DHC) in solid phase enzyme immunoassay was evaluated. The assay (by means of ELISA) is based on competition for the antibody between free antigen and antigen adsorbed to polystyrene (PJ Hogg et al., Mol. Immunol., 24:797–801, (1987)). The assay follows the general procedure in which ELISA plates were first coated with DHC at 10 µg/ml in 100 µl of coating buffer and incubated overnight at 4° C. Next day the excess of antigen was removed by washing each well 4 times with TS-Tween™. Reaction mixtures (100 µl/well) containing 100 ng/ml (0.65 nM) 3–48 $G_5C_7$ lot #2 IgG and DHC lot #15 (0–15 µM) in 20 mM Tris/HCl, 0.5M NaCl, pH 7.4 were placed in half of the coated wells, in triplicates. To the remaining wells, which were used for analysis of the interaction between IgG and immobilized DHC in the absence of soluble antigen was added the monoclonal 3–48 IgG (100 µl, 0–65 µM) in 20 mM Tris/HCl pH 7.4, 0.5M NaCl. After incubation at 37° C. for 1 hour, the plates were washed 4 times with TS-Tween prior to the addition of peroxidase-labeled polyclonal antibody directed to IgG+IgM (H+L) for a further 1 hour at 37° C. Excess second antibody was then removed by washing, peroxidase substrate added and absorbance measured at 450 nm. Affinity constant $K_{AS}$ was measured from the formula:

$$\frac{K_{AS}}{(1+2K_{AS}m_A)} = \text{slope of the curve representing binding of antibody in the presence of free antigen.}$$

Where $K_{AS}$ is slope of the curve described by:

$$\frac{A_{450\,nm}}{mA} \quad \frac{(Ab \text{ bound to matrix in the absence of free antigen})}{(\text{concentration of added antibody in uM})}$$

Following are Affinity constant values obtained for:

| Antigen | IgG | F(ab')$_2$ |
| --- | --- | --- |
| Human ventricular myosin heavy chains | $3.33 \times 10^8 M^{-1}$ | ND |
| Human skeletal muscle myosin | $1.06 \times 10^8 M^{-1}$ | ND |
| Canine cardiac myosin heavy chains | $2.06 \times 10^8 M^{-1}$ | $1.21 \times 10^8 M^{-1}$ |
| Human atrial myosin heavy chains | $1.48 \times 10^8 M^{-1}$ | ND |

3. Determination of the isoelectric point of 3–48 IgG$_1$

The isoelectric point (pI) of anti-myosin antibody was determined by isoelectrofocusing (IEF) in Pharmacia's Phast Gel™ IEF 3–9 medium in a pre-cast homogenous polyacrylamide gel containing Pharmalyte™ carrier ampholytes in the 3 to 9 pH range. When the immunoglobulin sample was applied at either cathodal or anodal end, its pI was between 6.85 and 6.55, while when applied in the middle of the gel, it was closer to 6.55.

4. Immunospecificity and cross-reactivity of the antibody 4.1. ELISA

The immunologic potency of the antibody of the present invention towards its target antigen, ventricular myosin heavy chains, and cross-reacting antigen, skeletal muscle myosin heavy chains, was quantitated by antibody titration and measurement of an affinity constant in ELISA.

Briefly, antigens were immobilized on polystyrene microtiter plates (Immulon I™, Dynatech Labs) at a concentration of 10 µg/ml in 0.1M sodium carbonate/bicarbonate buffer, pH 9.6 overnight at 4° C. Before use, the plates were washed and incubated for 1 hour at 37° C. with 1% low-fat powder milk in Tris-saline (TS). Antibody dilutions in TS containing 1% milk were incubated at 37° C. for 1 hour. After washes, the plates were incubated with peroxidase-conjugated anti-mouse IgG (H+L) diluted in TS-milk for 1 hour at 37° C., then washed, and the enzyme activity revealed with o-phenylenediamine (Sigma) at 1 mg/ml in 0.1M sodium citrate-citric acid buffer, pH 5.0, containing 0.03% $H_2O_2$. The color was read after 30 minutes in an automatic reader using interference filter of 450 nm.

Typical sigmoid serial dilution ELISA curves were obtained for all antigens tested: human cardiac and skeletal myosin, canine cardiac myosin, porcine, bovine, rabbit and chicken skeletal muscle myosin, chicken gizzard myosin. The IgG of the present invention has the highest affinity for human skeletal myosin, and then for human cardiac, bovine skeletal, canine cardiac, porcine skeletal and the lowest affinity for rabbit skeletal muscle myosin. There was no reactivity towards chicken gizzard nor chicken skeletal muscle myosin.

The antibody of the present invention was also found to react with human atrial and ventricular myosin chains (HVHC, HAHC), human skeletal myosin heavy chains (SkM), and canine ventricular myosin heavy chains (DHC) but not with atrial or ventricular myosin light chains in ELISA (FIG. 1). Thus, immunoglobulin reacts with α- and β-heavy chains of myosin, since human ventricular myosin is composed primarily of the β-type of heavy chains that share antigenic determinants with slow skeletal muscle myosin heavy chains, and human atrium of the α-type primarily.

Figure 2:
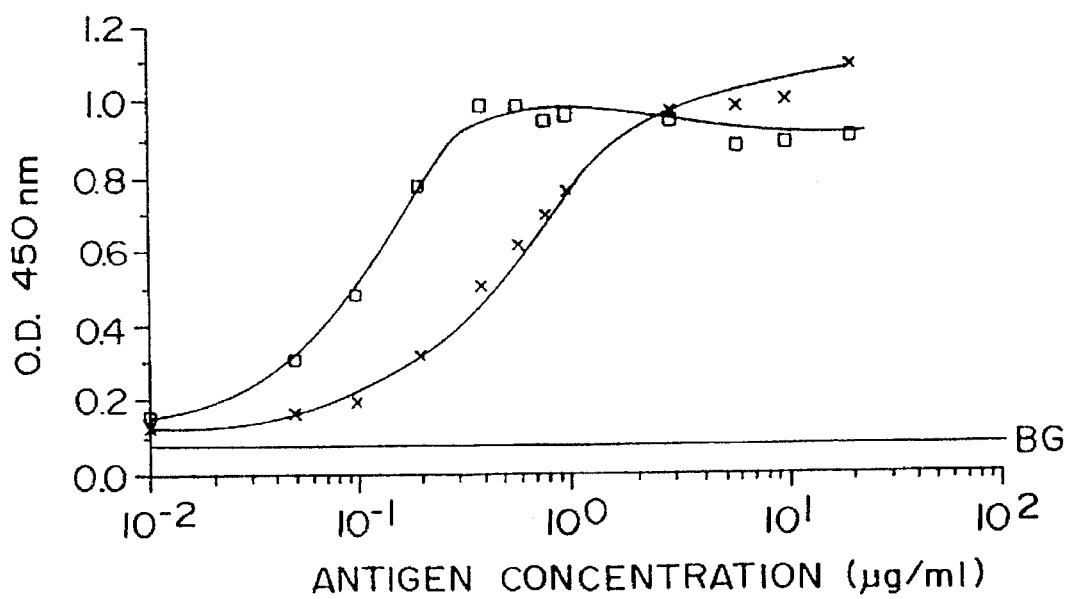
FIG. 2 shows the antigen concentration standard curves for human cardiac muscle myosin heavy chains (CHC) and human skeletal muscle myosin (SkM) in ELISA.

The potency of the McAb was also on occasion quantitated by constructing antigen concentration curves for which microtitration plates were coated with ascending concentrations of antigen and subsequently incubated with the IgG at the concentration equivalent to 50% of its maximum binding to the corresponding antigen. Typical antigen concentration curves are presented in FIG. 2.

Microtitration plates were coated with rising concentrations of either HVHC (x—x) or SkM (□—□) and incubated with the IgG$_1$ concentrations representing 50% of maximum binding (60 ng/ml for HVHC and 40 ng/ml for SkM). The bound antibody was detected by incubation with peroxidase labeled anti-mouse IgG.

In case of SkM, antibody saturation point is achieved with 0.4 ug/ml of SkM while for HVHC saturation point is reached with about 4 ug/ml of HVHC.

Unexpectedly, the 3–48 $G_5C_7$ antibody (ATCC HB9916) recognizes α and β-type heavy chains of LMM fragment of cardiac myosin and thus reacts with LMM fragment of cardiac myosin (Table 1).

TABLE 1

Binding of 3-48 monoclonal antibody to myosin fragments

| | Binding in ELISA (OD$_{450\,nm}$) | | |
| --- | --- | --- | --- |
| Fragment type | Ventricular myosin | Atrial myosin | Skeletal myosin |
| LMM[1] | 1.8 | 1.7 | 1.9 |
| HMM[1] | 0.09 | 0.08 | 0.09 |
| Native myosin | 1.8 | 1.7 | 1.9 |

To obtain LMM and HMM fragments, human ventricular, atrial or skeletal muscle myosin was obtained as described in the above section I and dialyzed against 0.5M KCl, 0.05M $K_2HPO_4$, pH 6.5 and protein concentration adjusted to 20 mg/ml. Trypsin was added to a final concentration of 0.05 mg/ml (1 ml of 0.05% trypsin in 0.001N HCl to 10 ml of myosin) and incubated at room temperature for 5 minutes, stirring. The digestion was terminated by raising pH to neutral with 1M Trizma™. To precipitate LMM, the digestion mixture was dialyzed against 0.02M KCl, 0.01M $K_2HPO_4$ pH 6.5, 0.001M DTT and LMM separated from HMM by centrifugation at 25,000 rpm for 60 min. LMM precipitate was dissolved in 0.5M KCl, 0.05M $K_2HPO_4$, pH 6.5. ELISA was performed as herein described. Namely, the microtitration plates were coated with 100 µg/well of antigens in carbonate/bicarbonate buffer pH 9.6 overnight at 4° C. The unbound antigen was washed off 4 times with Tris buffered saline pH 7.4 (TS), 0.05% Tween 20™ (TS-Tween) and the remaining binding sites saturated with 1% bovine serum albumin (250 µl/well) in TS for 1 hour at 37° C. After brief washing, the wells were incubated with 100 µl of 3–48 IgG (produced by hybridoma ATCC HB9916) at 50 ng/ml of TS for 1 hour at 37° C. The unbound antibody was washed off four times with TS-Tween™ and horseradish peroxidase-conjugated anti-mouse IgG+IgM antiserum added (100 µl/well) for further 1 hour incubation at 37° C. The colorimetric reaction was developed upon the addition of 30%

H₂O₂ at 1 µl/1 ml in 0.1M sodium citrate buffer pH 5.0 containing 0.1% o-phenylenediamine dihydrochloride, and the absorbance read at 450 nm.

The immunospecificity of 3-48 antibody (ATCC HB9916) towards LMM and not HMM was also true when LMM was prepared by chemotrypsin digestion of myosin. The method of Weeds et al. (Nature, 257:54 (1975)) was essentially followed.

Briefly, α-chemotrypsin solution (0.05% α-chemotrypsin in 0.001N HCl) was added to a final concentration of 0.05 mg/ml to 1.8% myosin in 0.5M KCl, 0.05M K₂HPO₄ solution, pH 6.5. The solution was stirred for 10 minutes at room temperature and digestion stopped by the addition of PMSF inhibitor to a final concentration of 0.3 mM. To separate HMM from LMM and undigested myosin, the digestion mixture was dialyzed against 0.02M KCl, 0.01M K₂HPO₄ pH 6.3, 0.001M DTT. HMM was separated by centrifugation at 20,000 rpm (Sorvall™ RC5C, rotor 05) for one hour.

Figure 3:
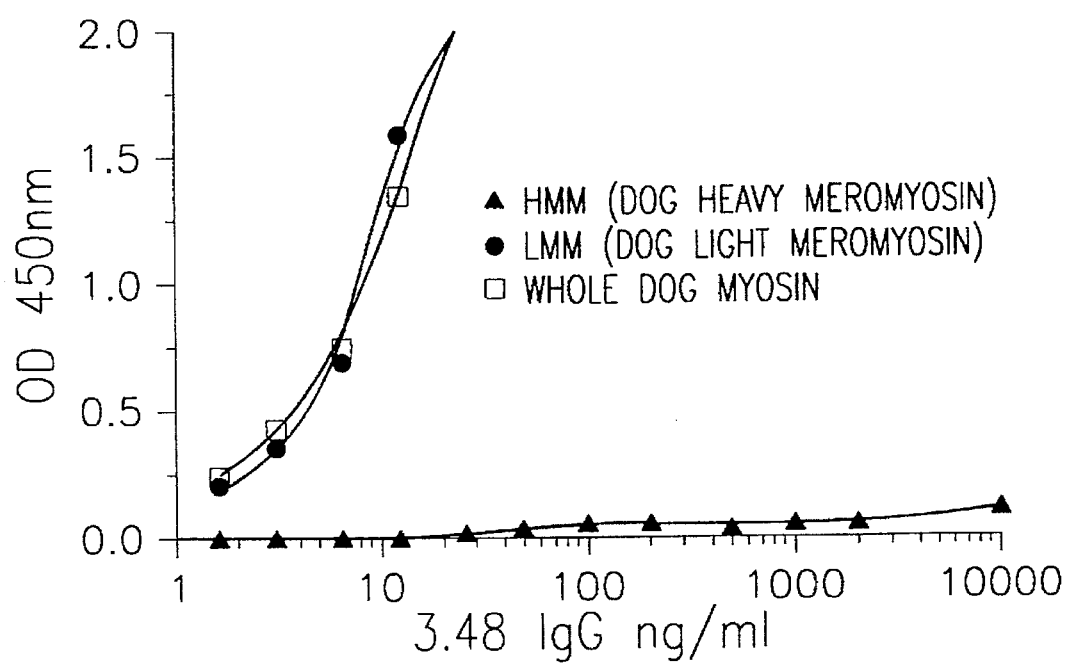
FIG. 3 shows the antibody reaction curves assayed in ELISA against light and heavy meromyosin fragments of canine cardiac myosin.

For ELISA, microtitration plates were coated with dog cardiac heavy and light meromyosin and dog whole cardiac myosin at a concentration of 10 µg/ml. The remaining binding sites were quenched with 1% TS-milk and wells incubated with different concentrations of 3-48 IgG (1-10, 000 ng/ml) for 1 hour at 37° C. Unbound IgG was washed off. The bound mouse IgG was detected with peroxidase labeled goat-anti-mouse IgG antiserum. Peroxidase substrate in o-phenylenediamine solution was added and absorbance read at 450 nm (FIG. 3).

4.2 Immunohistochemical staining of tissue sections with the antibody of the present invention.

Cryostat cuts of either human or animal fresh autopsy tissues were prepared on gelatinized slides and incubated with the present antibody at various dilutions in PBS for 1 hour at room temperature. The slides were washed in PBS and incubated for an additional one hour (after quenching of endogenous peroxidase with 0.3% H₂O₂ in methanol) with either fluorescein or peroxidase conjugated F(ab')₂ fragments of goat anti-mouse IgG. After washing as above, the slides were observed under either the fluorescence or light microscope.

Figure 4:
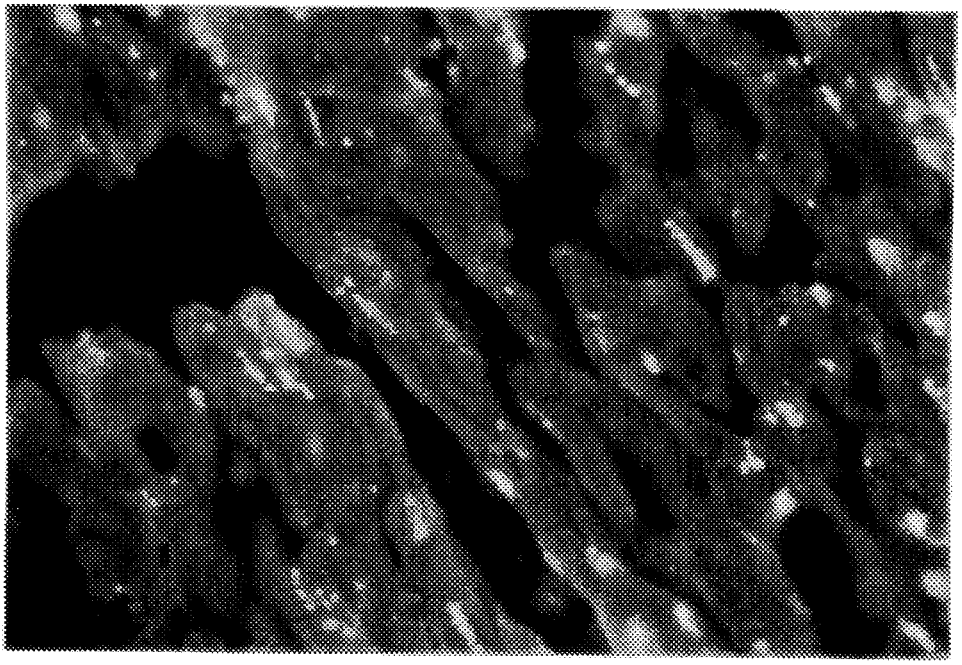
FIG. 4 shows the immunofluorescein staining of human cardiac ventricular muscle with 3–48 antibody fragments.
Figure 5:
FIG. 5 shows the immunofluorescein staining of human skeletal muscle with 3–48 IgG.

The antibody stained only striated muscle fibers in both atria and ventricles of human and animal hearts, as well as skeletal muscle fibers (FIG. 4). On longitudinal cryosections, the staining was restricted to the A bands of a myofibril, indicating that the antibody recognizes only myosin (S. Lowey, Med. Sci. Sport. Excer., 18, 284-291, (1986)) (FIG. 5). No staining was observed with other tissue antigens.

When incubated with human or rat cardiac myocytes in culture, the 3-48 antibody stained only cytoplasm and not nuclei or fibroblasts.

Since human atrial muscle contains also β-chain, as well as human ventricular muscle contains also α-chain, neither of those muscles can be considered a source of pure α- or β-heavy chains. To prove beyond doubt that the antibody 3-48 recognizes both α- and β- chains, cryocuts of rat hearts at various developmental or physiological stages were prepared.

It has been shown (C. A. Dechesne et al., J. Cell Biology, 105: 3031-3037 (1987)) that ventricles of:

- 20 to 25 day old Wistar male rats are composed of only αα-homodimers,
- 6 month old Wistar male rats contain both homo and heterodimers of αα-, αβ- and ββ-heavy chains, and
- 7 month old Wistar male rats thyroidectomized at 3 months of age contain only ββ-homodimers.

If 3-48 antibody recognizes only α-chain it will not stain thyroidectomized rat ventricles while if it recognizes exclusively β-chain it will not stain 20-25 day old rat ventricles.

The antibody was found to stain (by indirect immunofluorescence) all three types of ventricular tissue sections equally well, indicating that 3-48 antibody has been raised to common epitopes on α- and β-myosin heavy chains (Sikorska et al., Nucl. Med. Biol., 17:567-584 (1990)).

4.3 Immunodetection on Western blots

Sodium dodecyl sulfate-polyacrylamide gel electrophoresis (SDS-PAGE™) was performed on 8% acrylamide bisacrylamide running gel with 5% stacking gel in a Trisglycine discontinuous buffer system of Laemmli (Laemmli, Nature, 227, 680-685, (1970)) in a vertical slab gel apparatus. The electrophoretically resolved proteins were transferred at 35 V for 4 hours in 25 mM Tris, 192 mM glycine, 20% methanol, pH 8.3 to nitrocellulose sheets according to the method of Towbin (Towbin, H. et al., Proc. Natl. Acad. Sci., 76, 4350-4354, (1979)).

The remaining binding sites on nitrocellulose were quenched by overnight incubation at 4° C. in 5% BSA in TS. The blots were then incubated for 3 hr at room temperature, while shaking, with 3-48 antibody diluted in TS-1% BSA and then for 2 hr with peroxidase conjugated anti-mouse IgG. The enzymatic reaction was carried out by over-laying the strips with 0.03% H₂O₂ in diaminobenzidine at 1 mg/ml TS. Each of the steps was followed by extensive washing with TS-Tween 20™). Proteins electrotransferred to nitrocellulose were visualized by staining with 0.1% amido black in 45% methanol, 7% acetic acid and destained in the same solvent.

When atrial, ventricular and skeletal muscle myosin subunits were separated by SDS-PAGE™ and transferred to nitrocellulose, the 3-48 antibody reacted specifically with only the 200 kd band, corresponding to the myosin heavy chain (Sikorska et al., Nucl. Med. Biol., 17:567-584 (1990)).

In summary, the monoclonal antibody is myosin α- and β-heavy chain specific. On Western blots and in ELISA it reacts with purified heavy chains of atrial and ventricular human myosin, and more specifically with light meromyosin fragment of myosin. It binds to A-band of a thick filament of cardiac and skeletal muscle myosin as determined by indirect immunofluorescence on cryostat tissue sections, and indirect immunoperoxidase staining of Carnoy fixed tissues. It stains human and canine myocytes in culture as determined by indirect immunofluorescence.

It cross-reacts strongly with β-heavy chain of slow human skeletal muscle myosin but it neither binds with human myosin light chains nor smooth muscle myosin. It cross-reacts with canine, porcine, bovine, rabbit, sheep and rat α- and β-heavy chains of cardiac myosin and β-chain of skeletal myosin. Other animal species were not tested. The antibody does not cross-react with any other than myosin human tissue antigens or blood cells.

5. Karyotypic analysis

Hybridoma cells 3-48 G₅C₇ were further characterized by analysis of the mobility of glucose 6-phosphate dehydrogenase (G₆PD), nucleoside phosphorylase (NP), lactate dehydrogenase (LD), and malate dehydrogenase (MD) enzymes and by Giemsa banded chromosome analysis.

A. Isoenzyme Analysis of Cell Line ATCC HB9916

Electrophoretic mobilities of enzymes G₆PD, NP, LD, and MD present in an extract prepared from 3-48 G₅C₇ cells were comparable to those of a mouse cell preparation. No extra bands were found that would suggest the presence of another cell species.

B. Cytogenetic Analysis of ATCC HB9916

1. Chromosome count per 100 metaphases

The distribution of chromosome numbers found in the 100 metaphases analyzed for cell line 3–48 $G_5C_7$ is shown in Table 2. The chromosome count range from 47 to 93 chromosomes per metaphase.

TABLE 2

| Distribution of chromosome numbers in the 100 metaphases analyzed for cell line ATCC HB9916 | |
| --- | --- |
| Number of Chromosomes | Number of Metaphases |
| 47 | 1 |
| 67 | 2 |
| 70 | 1 |
| 71 | 1 |
| 72 | 2 |
| 73 | 6 |
| 74 | 2 |
| 75 | 10 |
| 76 | 3 |
| 77 | 11 |
| 78 | 8 |
| 79 | 5 |
| 80 | 17 |
| 81 | 3 |
| 82 | 7 |
| 81 | 3 |
| 82 | 7 |
| 83 | 10 |
| 84 | 1 |
| 85 | 3 |
| 86 | 3 |
| 87 | 2 |
| 90 | 1 |
| 93 | 1 |

2. Chromosome Aberration Data

The chromosome aberration data for the 50 metaphases examined is summarized in Table 3.

TABLE 3

| Chromosome aberration data for cell line ATCC HB9916 | | | | | | |
| --- | --- | --- | --- | --- | --- | --- |
| TYPE OF ABERRATION | | | | | | |
| Chromatide | | Chromosome | | Severely | No. Cells | Total No. |
| Deletion | Interchg. | Deletion | Interchg. | Damgd. Cell | Aberrant | Aberration |
| 6 | 0 | 1 | 0 | 0 | 7 | 7 |

Cells analyzed = 50
Aberrations = 7
Cells with Aberrations = 7
% Cells with Aberrations = 14
Aberrations/Cell = 0.14

Seven chromosome aberrations were found in the 50 cells analyzed with 14 percent cells aberrant.

3. Giemsa Banded Chromosome Analysis/Karyotypes

Five karyotypes were prepared. Cytogenetic examination shows that the cell line is of "mouse" origin.

Cell line ATCC HB9916 showed a wide and highly variable distribution of normal chromosomes, chromosomal rearrangements, and markers. Due to such variability in the karyotype, all unidentifiable chromosomes as well as all chromosomes containing rearrangements were collectively classified as markers. Markers ranged in numbers from 58–64 in the 5 cells karyotyped.

TABLE 4

Distribution of normal chromosomes & number of marker chromosomes
in the 5 karyotypes analyzed for cell line ATCC HB9916

No. of Copies of Normal Chromosomes and
Unidentified Karyotype Marker Chromosomes (M)

| No. | 1 | 2 | 3 | 4 | 5 | 6 | 7 | 8 | 9 | 10 | 11 | 12 | 13 | 14 | 15 | 16 | 17 | 18 | 19 | X | Y | M |
|---|---|---|---|---|---|---|---|---|---|---|---|---|---|---|---|---|---|---|---|---|---|---|
| 1 | 0 | 2 | 2 | 0 | 0 | 2 | 1 | 0 | 1 | 2 | 2 | 1 | 2 | 2 | 0 | 0 | 1 | 1 | 0 | 1 | 0 | 61 |
| 2 | 2 | 1 | 2 | 0 | 1 | 0 | 1 | 0 | 2 | 1 | 2 | 0 | 0 | 2 | 0 | 1 | 0 | 0 | 3 | 1 | 0 | 64 |
| 3 | 2 | 2 | 1 | 0 | 1 | 1 | 1 | 0 | 2 | 2 | 2 | 0 | 1 | 1 | 0 | 0 | 0 | 0 | 1 | 0 | 0 | 58 |
| 4 | 3 | 4 | 0 | 0 | 1 | 0 | 1 | 1 | 2 | 1 | 2 | 0 | 2 | 1 | 2 | 0 | 2 | 0 | 1 | 0 | 0 | 61 |
| 5 | 2 | 3 | 1 | 0 | 2 | 0 | 0 | 0 | 2 | 3 | 3 | 0 | 1 | 2 | 1 | 0 | 1 | 0 | 0 | 0 | 0 | 62 |

No attempt was made to describe the origin of the numerous chromosomal rearrangements due to the degree of variability of the karyotype.

Normal chromosomes were found as absent, present, or in multiple copies depending on the cell analyzed. Chromosome #4 and the Y chromosome were absent in all karyotypes.

6. Molecular weight of IgG
acc. to SDS-PAGE
  under ME reduced conditions: 153.8 kd 49.7 kd heavy chain 27.2 kd light chain
  no ME reduction: 253.7 kd
acc. to gel filtration: 170 kd 7. Molecular weight of F(ab')$_2$ fragment
acc. to SDS-PAGE
  under ME reduced conditions: 120 kd 30.5 kd heavy chain 29.5 kd light chain
  no ME reduction: 127 kd
acc. to gel filtration: 80 kd 8. Molecular weight of Fab' fragment
acc. to SDS-PAGE
  under ME reduced conditions: 46.5 kd 30.5 kd heavy chain 29.5 kd light chain
  no ME reduction: 51.5 kd
acc. to gel filtration: 39.0 kd III- Radioimmunoscintigraphy with the antibody of the present invention 1. Radioimmunolocalization of labeled antibody in animal model of myocardial infarction 1.1 $^{125}$I-labeled antibody $^{125}$I-labeled antibody was tested in a rat myocardial infarct (MI) model. Myocardial ischemic injury was induced with isoproterenol and resulted in increased cardiac uptake of Tc-99m-pyrophosphate (PYP) which is selectively retained by necrotic myocardium.

Figure 6:
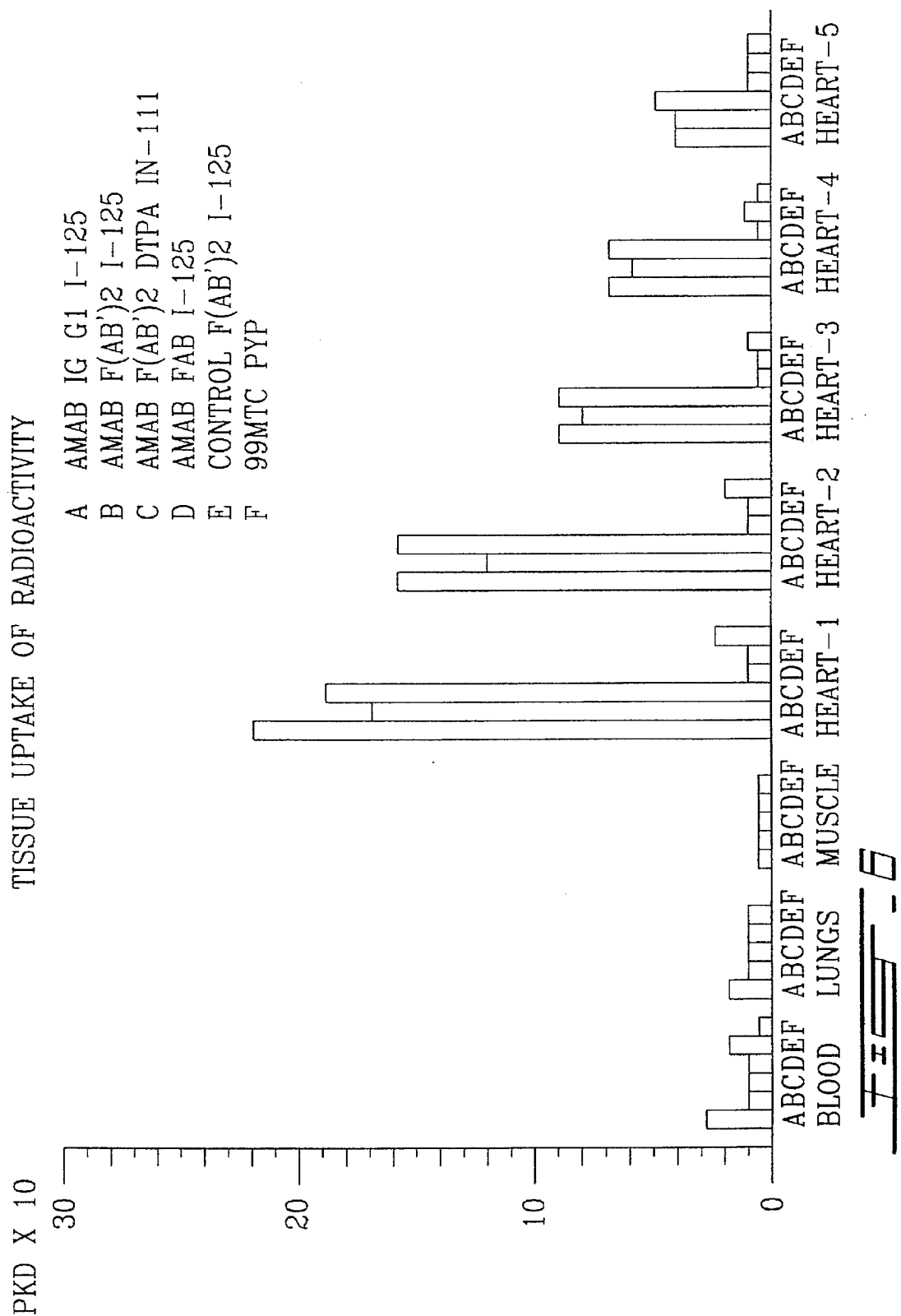
FIG. 6 shows the tissue uptake of the labeled antibodies and fragments in PKD (percent/kg/dose)
Figure 7:
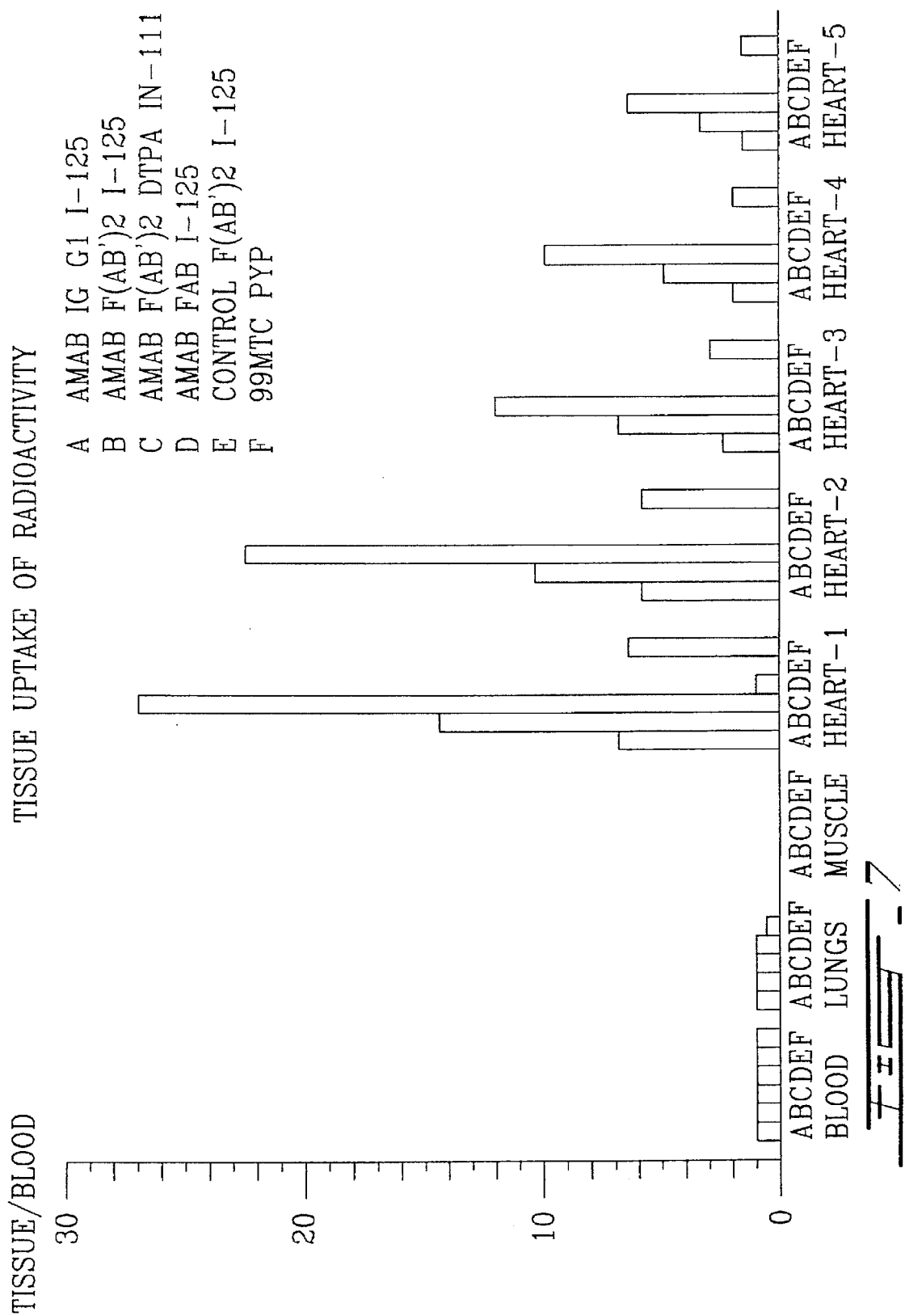
FIG. 7 shows the tissue uptake of the labeled antibodies and fragments in a tissue to blood ratio.

The IgG$_1$, and its Fab' and F(ab')$_2$ fragments as well as F(ab')$_2$ fragments from normal mouse IgG were $^{125}$I-labeled by iodogen method. Rats were injected twice with isoproterenol and four hours after the second injection they were innoculated i.v. with labeled antibody or $^{99m}$Tc pyrophosphate. The animals were sacrificed after 20 hours and their hearts excised and blood, lung and skeletal muscle samples were collected. The data (Tables 5 and 6; FIGS. 6 and 7) clearly indicate that $^{125}$I-labeled antibody F(ab')$_2$ fragments exhibit the best retention in the infarcted rat heart, with high tissue to blood ratio, twice higher than the one for $^{99m}$Tc PYP.

TABLE 5

| | Tissue uptake in PKD × 1000a (S.D.)b | | | | | | | |
|---|---|---|---|---|---|---|---|---|
| No. Compounds | BLOOD | LUNG | MUS. | T1 | T2 | T3 | T4 | T5 |
| 1-AMab IgG$_1$ | 287 | 208 | 37 | 2221 | 1599 | 926 | 675 | 420 |
| ($^{125}$I) | (28) | (121) | (22) | (578) | (308) | (247) | (241) | (150) |
| 2-AMab F(ab')$_2$ | 121 | 97 | 22 | 1698 | 1205 | 749 | 606 | 398 |
| ($^{125}$I) | (29) | (40) | (6) | (823) | (437) | (421) | (313) | (173) |
| 3-AMab F(ab')$_2$ | 68 | 76 | 26 | 1868 | 1583 | 871 | 736 | 532 |
| DTPA ($^{111}$In) | (18) | (3) | (1) | (585) | (473) | (325) | (335) | (235) |
| 4-AMab Fab- | 95 | 67 | 16 | 111 | 82 | 57 | 51 | 58 |
| ($^{125}$I) | (17) | (28) | (4) | (33) | (31) | (20) | (18) | (16) |
| 5-Control | 189 | 111 | 16 | 93 | 85 | 79 | 78 | 82 |
| F(ab')$_2$($^{125}$I) | (32) | (17) | (3) | (60) | (40) | (28) | (26) | (30) |
| 6-$^{99m}$Tc PYP | 35 | nil | nil | 225 | 182 | 113 | 64 | 62 |
| | (12) | nil | nil | (37) | (48) | (61) | (33) | (18) | a PKD, percent kg dose, (($\mu$Ci/g organ)/($\mu$Ci(dose/kg body wt))) × 100.
b standard deviation
c AMab, anti-myosin antibody

TABLE 6

| No. Compounds | Tissue to blood ratio (S.D.)a | | | | | | | |
|---|---|---|---|---|---|---|---|---|
| | BLOOD | LUNG | MUS. | T1 | T2 | T3 | T4 | T5 |
| 1-AMab IgG$_1$ | 1 | 0.71 | 0.13 | 7.75 | 5.55 | 3.19 | 2.31 | 1.46 |
| ($^{125}$I) | (0) | (0.36) | (0.06) | (2.01) | (0.80) | (0.52) | (0.56) | (0.46) |
| 2-AMab F(ab')$_2$ | 1 | 0.78 | 0.18 | 15.35 | 10.69 | 6.74 | 5.38 | 3.38 |
| ($^{125}$I) | (0) | (0.13) | (0.02) | (8.94) | (5.12) | (4.80) | (3.63) | (1.68) |
| 3-AMab F(ab')$_2$ | 1 | 1.18 | 0.41 | 27.45 | 23.36 | 12.75 | 10.73 | 7.62 |
| DTPA ($^{111}$In) | (0) | (0.30) | (0.12) | (4.03) | (3.39) | (2.83) | (3.18) | (1.77) |
| 4-AMab Fab- | 1 | 0.69 | 0.17 | 1.15 | 0.84 | 0.59 | 0.52 | 0.6 |
| ($^{125}$I) | (0) | (0.15) | (0.01) | (0.17) | (0.15) | (0.10) | (0.08) | (0.09) |
| 5-Control | 1 | 0.59 | 0.09 | 0.47 | 0.44 | 0.41 | 0.41 | 0.43 |
| F(ab')$_2$($^{125}$I) | (0) | (0.02) | (0.01) | (60) | (0.13) | (0.08) | (0.07) | (0.09) |
| 6-$^{99m}$Tc PYP | 1 | nil | nil | 6.75 | 5.56 | 3.48 | 2.01 | 1.85 |
| | (0) | nil | nil | (1.49) | (2.30) | (2.30) | (1.27) | (0.74) | a standard deviation

There is no accumulation of antibody or its fragments in the normal heart or skeletal muscle nor is there any binding of the non-immune mouse IgG in the infarcted area.

1.2 $^{111}$In-labeled antibody 1.2.1 MI (Myocardial infarction) rat model

Protein labeling complex was obtained by reacting the antibody (135 μg) with an excess of DTPA anhydride at 4° C. for 5 hours, with occasional stirring, whereafter excess DTPA was removed via centrifugation of the reaction mixture over a packed G-50 Sephadex™ column (0.8 ml in a 1 ml seringe) in 0.9% saline.

For labeling, the commercially obtained $^{111}$In chloride was converted to the acetate by mixing $^{111}$In chloride with a 0.5M sodium acetate solution (pH 4). The DTPA-protein complex was added to the $^{111}$In acetate solution (200 uCi), and left at room temperature for 1 hour. The mixture was loaded on a Sephadex G-50™ column (1×20 cm) and eluted with a 0.05M Hepes™, 0.9% saline buffer. The labeled antibody (labeling efficiency 25–40%) was collected in the 6 to 8 ml fraction, and was detected by its UV absorption at 280 nm. The labeled antibody was filtered over a 0.22 um Millipore™ filter prior to injection in the animals. Retention data of the labeled products in the various tissue samples are summarized in Table 5, tissue to blood ratios are presented in Table 6. Data are also presented as bar plots to facilitate comparison of the various products (FIGS. 6 and 7).

In this animal model, the degree of heart infarction is the highest in the tip slice T$_1$, with gradual diminishing of the infarction from T$_1$–T$_5$ and with the cranial slice T$_5$ almost appearing as unaffected healthy tissue. Accordingly, T$_5$ may be taken as an internal control of the healthy heart muscle.

It may be seen from the data (Tables 5 and 6) that the $^{125}$I and $^{111}$In-labeled AMab F(ab')$_2$ fragment exhibits the best retention in the infarcted rat heart, with a 2 to 4× higher tissue to blood ratio as compared to $^{99m}$Tc PYP. The $^{111}$In DTPA-AMab F(ab')$_2$ probably due to a lower blood retention and a somewhat better tissue uptake reached much higher tissue to blood ratio than its $^{125}$I-labeled counterpart.

Since the $^{111}$In labeling efficiency of 25–40% obtained in the preliminary experiment is unsatisfactory for human use due to excess of free isotope, the conditions of labeling had to be optimized and standardized.

Thus, sterile, apyrogenic and heavy metal ions free antibody F(ab')$_2$ fragments of 3-48 IgG were covalently linked with DTPA by the cyclic anhydride method at the molar ratio of 1:100. An aliquot of 0.5 mg DTPA-antibody F(ab')$_2$ was dissolved in 100 μl PBS, and 1.8 ml of 0.1M citrate (pH 5.0) was added. To this mixture, 2 mCi of $^{111}$In was added, and incubated at room temperature for 10–15 minutes. A small aliquot (0.01 ml) was used to determine labeling efficiency by ascending thin layer chromatography on cellulose acetate sheets developed in 0.1M citrate, pH 5.0. The ratio of radioactive counts at the origin to that of the solvent front was used to compute labeling efficiency. Samples with 85% incorporation of $^{111}$In determined after 15–30 minutes of incubation at room temperature were considered usable. Labeling efficiency of 90 and 95% have been achieved.

The immunologic specificity of DTPA chelated antibody fragments was tested in an inhibition ELISA and by determining an affinity constant in ELISA. The chelated fragments were still reactive towards its antigen but their potency was reduced by 20%.

In summary, when radiolabeled with $^{125}$I or $^{111}$In, and injected i.v. into rats with isoproprenolol induced myocardial infarction four hours after infarct induction, the antibody localized only in the cardiac necrotic tissue. The label accumulation was proportional to infarct size and location was superior for F(ab')$_2$ fragments of immunoglobulin, when compared to intact molecule or Fab fragment. The maximum heart to blood ratio was 28:1.

1.2.2 MI dog model

The experimental infarctus was obtained by selective obstruction of a coronary artery with an artificially induced blood clot. The procedure is preferred over ligation since it does not require open chest surgery and allows for rapid recovery of the animal.

Adult female mongrel dogs (50–70 lb.) were used. Animals were pretreated with Rompun prior to the procedure. A venous infusion line was placed in the cephalic vein and the dog was infused with penthobarbital. A guide catheter was introduced in the femorai artery and brought under fluoroscopic control into the aortic root. The coronary anatomy was delineated angiographically and the guide catheter was introduced into the guide up to the coronary artery and microfibrillar collagen preparation (Avitene Alcon Lab. Inc., Forth Worth Tex., USA) was injected to block the artery. An injection of contrast agent was used to confirm the obstruction. The level of cardiac enzyme CPK in the blood was monitored before and at 5 and 20 h post infarctus. The animals were sacrificed 5 days post occlusion by bleeding under deep penthobarbital anesthesia. The heart was removed, washed and sent for pathologic examination and tetrazolium blue coloration.

Figure 8:
FIG. 8 shows the scintiscan of a dog infarcted heart.

The doses and intervals between artery occlusion and radiopharmaceutical administration were: 5 h for the Fab- and F(ab')$_2$-DTPA-$^{111}$In (2 mCi, 400 μg) and 48 h for $^{99m}$Tc-PYP (10 mCi). The intervals between radiopharmaceutical injection and imaging were: 5, 20 and 40 h for the $^{111}$In preparations and 3 h for the $^{99m}$Tc-PYP. Whole body planar scintigraphic studies in the dog gave good images of the necrotic myocardium 20 h post-injection with either $^{111}$In-labeled Fab or F(ab')$_2$ (FIG. 8). Earlier scans (5 h) gave a too high blood-background while later scans (40 h) did not improve the image obtained at 20–24 h.

One dog was sacrificed 20 h post-injection of F(ab')$_2$-DTPA-$^{111}$In and 3 h post-injection of $^{99m}$Tc-PYP. The heart was removed, cut in 1 cm thick slices perpendicular to the ventricular axis. The heart slices were imaged using a gamma camera with one window set on the 140 keV peak of $^{99m}$Tc and the other on the 247 keV peak of $^{111}$In. A small window opening (10%) was used to avoid spilling from the 178 keV gamma of $^{111}$In into the $^{99m}$Tc window imaging. The dog heart images suggest that the AMab derived preparations visualize necrotic zones only, in contrast with conventional $^{99m}$Tc-PYP preparations which visualize both ischemic and necrotic tissues. Another advantage of the antibody preparation over $^{99}$mTc-PYP is the absence of activity in the bones.

1.3 $^{99m}$Tc-labeled antibody

The usefulness of $^{111}$In-radiolabeled anti-myosin (AM) monoclonal antibody (Mab) for the evaluation of myocyte death has been demonstrated above. However the clinical utility of this radiopharmaceutical is limited by the unfavorable properties of the radioindium label. $^{99m}$Tc possesses better imaging and handling properties than $^{111}$In, but the more rigorous reaction conditions involved in $^{99m}$Tc-labeling has deterred its use for antibody labeling. Recently however, development of instant kit procedures for labeling monoclonal antibodies with $^{99m}$Tc, have made possible the clinical assessment of $^{99m}$Tc radiolabeled immunoradiopharmaceuticals including anti-myosin.

Pure 3–48 AM Fab' was radiolabeled with $^{99m}$Tc according to a regulated reduction method of RhoMed Inc. (U.S. Pat. Nos. 4,424,200 and 5,078,985). Briefly, AM(3–48)Fab' was pretinned by incubating the protein (8.3 mg/ml) with 5 mM stannous tartrate in 40 mM potassium hydrogen phthalate, 10 mM sodium potassium tartrate, pH 5.6 for 21 hr at room temperature. The excess tin was removed over a desalting column and the antibody fragment eluted in 37 mM inositol, 15.5 mM glycine, 40 mM potassium hydrogen phthalate, 10 mM sodium potassium tartrate, 1.25 mM stannous tartrate pH 5.6 aliquoted and lyophilized to yield kits containing 0.5 mg of protein per vial. The AM(3–48) Fab' kits (Cardio Vision™) were labeled with 0.5 ml of freshly eluted [$^{99m}$Tc]-pertechnetate (740–1110 MBq, 20–30 mCi) that was aseptically added to the shielded vial containing the antibody fragments and the mixture was allowed to react for 30 min. with occasional swirling.

On every occasion, over 95% radiolabeling yield based on protein bound $^{99m}$Tc with less than 1% of the radioactivity present in a colloidal form, was obtained.

Canine infarct model was induced as described above. The dogs were injected at the time intervals given in Table 7 with 0.5 mg, 629–740 MBq (17–20 mCi) of either $^{99m}$Tc-AM(3–48)Fab' (Cardio Vision™), $^{99m}$Tc-Pyrophosphate (Technescan™, PYP kit, Mallinckrodt U.S.A.), $^{99m}$Tc-Sestamibi (Cardiolite™ kit, (Dupont, U.S.A.) or $^{201}$Tl-Thallous Chloride (74 MBq; 2 mCi) (Dupont, U.S.A.). The images were recorded at 2, 6 and 12 hr following the injection of $^{99m}$Tc-AM(3–48)Fab' and at 4, 1 hr and 15 min. following the administration of $^{99m}$Tc-Pyrophosphate, $^{99m}$Tc-Sestamibi and $^{201}$Tl-Thallous chloride, respectively. Planar anterior left and right lateral scintigraphic images of the heart were recorded in digital format (128×128 matrix, 255 events per slots, 2×16 color scale) with a Picker Dyna-4 camera, with acquisition times ranging from 10 to 20 min., (25–100.10$^3$ counts per image). Care was taken to always position the dog heart in the same orientation relative to the camera by using the shoulder articulation, ribs and tip of the sternum as anatomical reference points. The head and neck area along with the abdomen were also imaged. The dogs were anesthetized throughout the imaging procedures.

Tomographic SPECT images were obtained with a Toshiba Model-602™ camera. A serie of 36 anterior projections were collected over 180° at 5° increment of 40 sec. each using a 64×64 matrix. Transaxial slices 5.5 mm thick (1 pixel) were reconstructed on a Star-4000™ imaging system by a back filtered projection method (Chesler ECT filter).

Figure 9A:
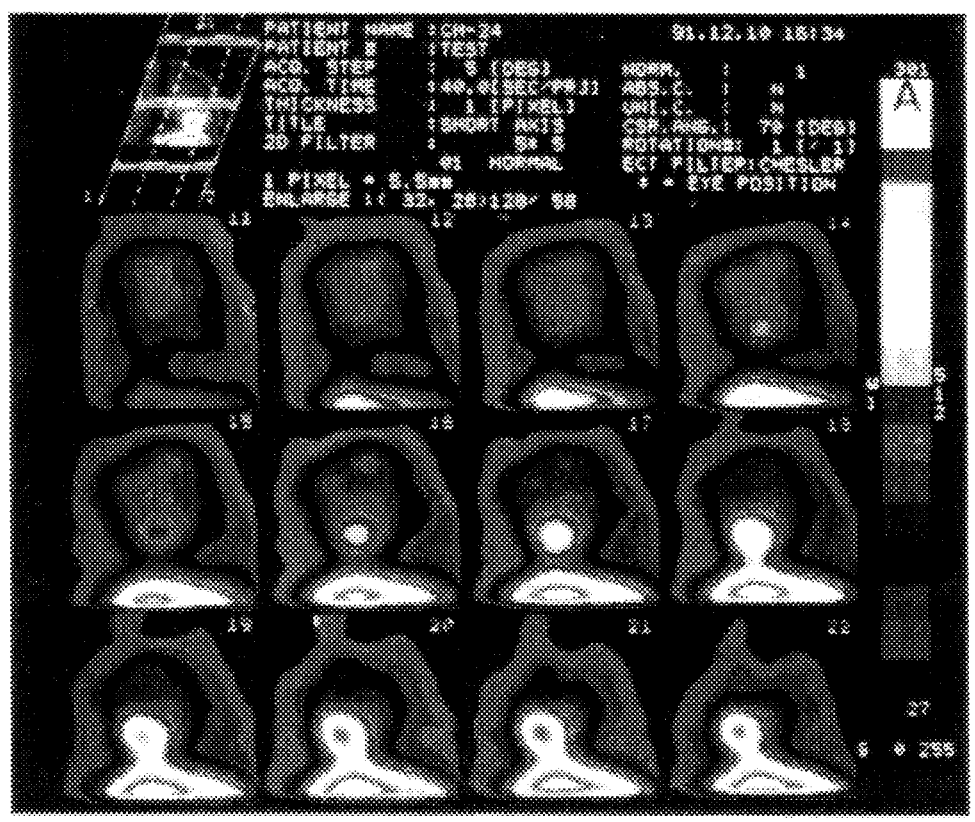
Figure 9C:
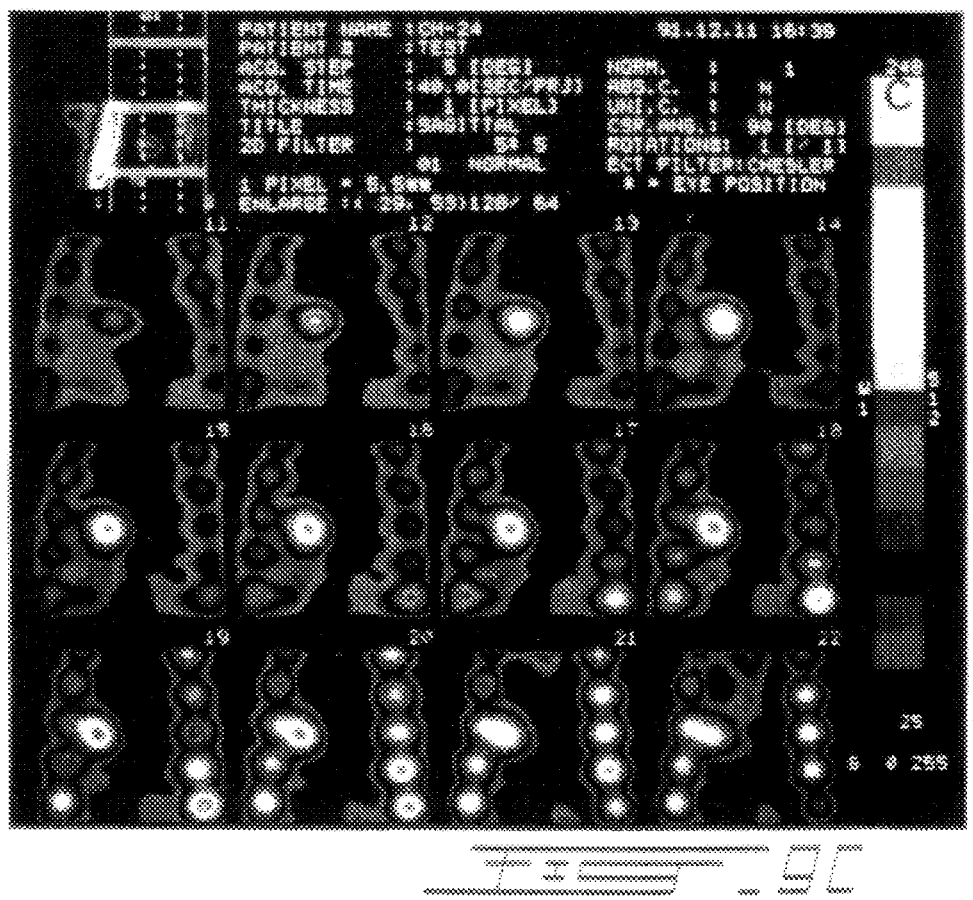

FIG. 9 shows SPECT imaging of an experimental canine heart infarct (dog #200). A: $^{99m}$Tc-Cardio Vision™ (Fab'); B: $^{99m}$Tc-Sestamibi (Cardiolite, Dupont); C: $^{99m}$Tc-Pyrophosphate (PYP, Mallinckrodt). The infarctus was induced by occlusion of the circonflex artery and extended from the tip of the heart to the right anterior portion of the heart. Images with $^{99m}$Tc-Fab' were taken the next day after induction of the infarctus, $^{99m}$Tc-Sestamibi and $^{99m}$Tc-Pyrophosphate images were taken at 1 day intervals thereafter. The dog was injected i.v. with 10–15 mCi of the radiopharmaceutical and the scans were taken 6 hours post-injection for A, 1 hour post-injection for B and 4 hours post-injection for C.

TABLE 7

| | | | Scintigraphic Imaging in the Dog | | | | | | |
|---|---|---|---|---|---|---|---|---|---|
| Dog | | Weight | | Time intervals between the infarction and the administration of the radiopharmaceuticals. | | | | | |
| No. | Sex | kg | Imaging | Day 1 | Day 2 | Day 3 | Day 4 | Day 6 | Day 21 |
| 82 | F | 32 | Planar | Fab' | PYP | | | | |
| 13 | F | 21 | Planar | Fab' | PYP | | | | |
| 41 | F | 24 | Planar | | Fab' | PYP | | | |
| 24 | F | 27 | SPECT | Fab' | PYP | | | MIBI | |
| 240 | F | 46 | Planar | Fab' | PYP | MIBI | | Thallium | |
| 200 | F | 30 | SPECT | | | Fab'/thallium | | | Fab' |

2. Radioimmunoscintigraphy with $^{99m}$Tc-labeled antibody fragments (Cardio Vision™) of patients with MI The antibody fragments of the present invention were radiolabeled with $^{99m}$Tc as described above. 40 patients with proven MI (22 Q-wave, 18 non Q-wave) were injected with $^{99m}$Tc-AM(20–25 mCi) between 5 hours and 7 days after the onset of acute chest pain. Three standard planar views were performed at 6 hours and at 24 hours post injection. Both sets of images were completed in 33 patients while 2 patients were imaged only at 6 hours, 3 patients only at 18 hours and one at 18 and 24 hours. One patient was not imaged. Vital signs and ECG were recorded and blood samples for hematology, biochemistry and human antimurine antibodies (HAMA) and urinalysis were obtained in all volunteers and patients.

No serious adverse reactions or side effects attributable to $^{99m}$Tc-AM have been reported. No volunteers or patients developed allergic reactions or significant increases in HAMA titers. Reading of $^{99m}$Tc-AM imaging was performed by 2 blinded experienced observers. The sensitivity of $^{99m}$Tc-AM in detection of MI was 100% (21/21) for Q-wave and 83.3% (15/18) for non Q-wave infarctions. The overall sensitivity was 92.3% (36/39). The 3 false-negative cases were infero-posterior MI. A certain degree of uptake focalization was seen in 26 out of 35 (74.2%) at 6 hours. At 24 hours, two patients (5.8%) did not show $^{99m}$Tc-AM uptake while 22 (64.7%) showed intense focal uptake, 7 (20.6%) moderate and 3 (8.9%) slight $^{99m}$Tc-AM uptake.

Figures 10A, 10B:
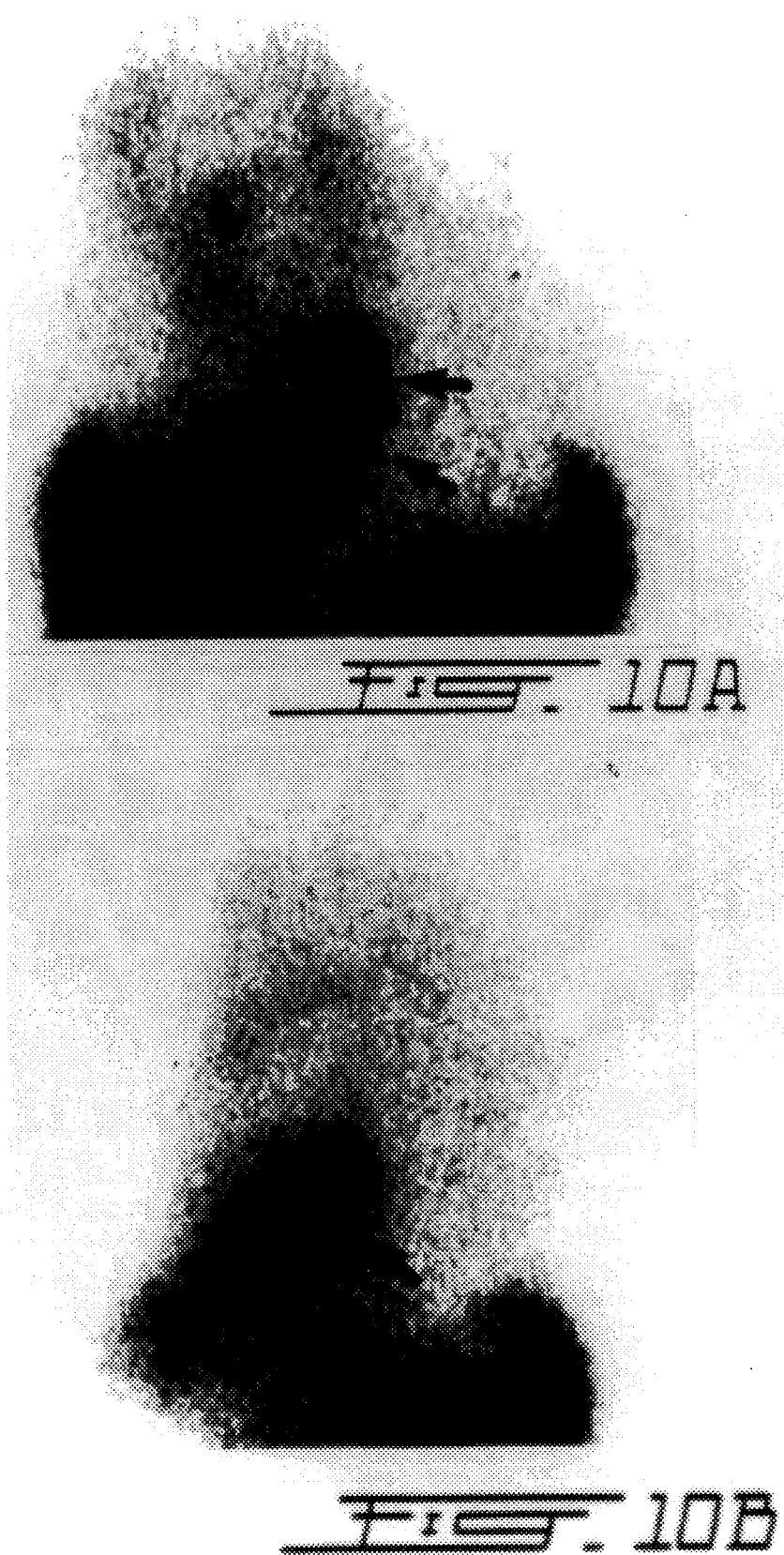
FIG. 10 shows images obtained 6 hr. after injection of $^{99m}$Tc-AM 3–48 fragments into a patient with postero-lateral Q-wave myocardial infarction, FIG. 10(A) 45° left anterior oblique, FIG. 10(B) left lateral views.

FIG. 10 shows images obtained at 6 hours after the injection of $^{99m}$Tc-anti-myosin in a patient with a postero-lateral Q-wave myocardial infarction (4 day-old). The site of acute necrosis is well delineated (arrows on the 45° left anterior oblique (A) and left lateral views (B).

In conclusion, $^{99m}$Tc-AM (3–48) imaging is safe and shows high sensitivity in detection of both Q-wave and non Q-wave MI even with early imaging (6 hours post i.v.). These promising results warrant further clinical investigation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A monoclonal antibody which is produced by the hybridoma deposited with the American Type Culture Collection (ATCC) having the accession number ATCC HB9916 or an antigen binding fragment thereof.

2. The hybridoma deposited with the ATCC having the accession number ATCC HB9916.

3. A method of diagnosing a myocardial infarction comprising:
   i) administering to a patient who has experienced myocardial cell necrosis or is suspected of same, a monoclonal antibody or antigen binding fragment thereof of claim 1 that is delectably labeled under conditions such that binding of said antibody or antigen binding fragment to in situ myosin fragments can occur with development of an image from which an evaluation of ventricular and atrial damage can be obtained, and
   ii) evaluating the image in i) to assess the presence of ventricular and atrial damage wherein the presence of ventricular and atrial damage is diagnostic of myocardial infarction.

4. The monoclonal antibody or antigen binding fragment thereof of claim 1 which is detectably labeled.

5. The monoclonal antibody or antigen binding fragment thereof of claim 4 which is detectably labeled with a radioisotope selected from the group consisting of 111-indium, 125-iodine, and 99m-technicium.

6. The monoclonal or antigen binding fragment thereof antibody of claim 5 wherein the radioisotope is 99m-technicium.

7. The antigen binding fragment of the monoclonal antibody of claim 1 wherein the fragment is selected from the group consisting of F(ab) and F(ab')$_2$.

8. A method of diagnosing a mvocard ial infarction comprising:
   i) administering to a patient who has experienced myocardial cell necrosis or is suspected of same, a monoclonal antibody or antigen binding fragment thereof, of claim 6 under conditions such that binding of said antibody or antigen binding fragment to in situ myosin fragments can occur with development of an image from which an evaluation of ventricular and atrial damage can be obtained, and
   ii) evaluating the image in i) to assess the presence of ventricular and atrial damage wherein the presence of ventricular and atrial damage is diagnostic of myocardial infarction.

9. A method of diagnosing a myocardial infarction comprising:
   i) administering to a patient who has experienced myocardial cell necrosis or is suspected of same, a monoclonal antibody or antigen binding fragment thereof, of claim 8 under conditions such that binding of said antibody or antigen binding fragment to in situ myosin fragments can occur with development of an image from which an evaluation of ventricular and atrial damage can be obtained, and
   ii) evaluating the image in i) to assess the presence of ventricular and atrial damage wherein the presence of ventricular and atrial damage is diagnostic of myocardial infarction.

10. A method of diagnosing a myocardial infarction comprising:
    i) administering to a patient who has experienced myocardiai cell necrosis or is suspected of same, an antigen binding fragment of the monoclonal antibody of claim 7 under conditions such that binding of said antibody or antigen binding fragment to in situ myosin fragments can occur with development of an image from which an evaluation of ventricular and atrial damage can be obtained, and
    ii) evaluating the innage in i) to assess the presence of ventricular and atrial damage wherein the presence of ventricular and atrial damage is diagnostic of myocardial infarction.

* * * * *